US009345947B2

(12) United States Patent
Harris et al.

(10) Patent No.: US 9,345,947 B2
(45) Date of Patent: *May 24, 2016

(54) EXERCISE FACILITY AND RELATED COMPUTER-GENERATED PERSONAL TRAINING SYSTEM AND METHOD

(71) Applicant: HAI Logan Gym, LLC, Logan, UT (US)

(72) Inventors: Robert D. Harris, Logan, UT (US); Blake Harris, Logan, UT (US)

(73) Assignee: HAI Logan Gym, LLC, Logan, UT (US)

(*) Notice: Subject to any disclaimer, the term of this patent is extended or adjusted under 35 U.S.C. 154(b) by 204 days.

This patent is subject to a terminal disclaimer.

(21) Appl. No.: 14/012,754

(22) Filed: Aug. 28, 2013

(65) Prior Publication Data

US 2014/0067097 A1   Mar. 6, 2014

Related U.S. Application Data

(60) Provisional application No. 61/828,489, filed on May 29, 2013, provisional application No. 61/816,510, filed on Apr. 26, 2013, provisional application No. 61/694,126, filed on Aug. 28, 2012.

(51) Int. Cl.
*A63B 71/06* (2006.01)
*G06F 19/00* (2011.01)
*G09B 19/00* (2006.01)

(52) U.S. Cl.
CPC ............ *A63B 71/06* (2013.01); *G06F 19/3481* (2013.01); *G09B 19/0038* (2013.01)

(58) Field of Classification Search
CPC ........... A63B 71/0619; A63B 71/0622; A63B 24/002; A63B 24/0075; G09B 19/0038; G06F 19/3481

See application file for complete search history.

(56) References Cited

U.S. PATENT DOCUMENTS

| | | | |
|---|---|---|---|
| 5,435,799 A | 7/1995 | Lundin | |
| 5,577,981 A | 11/1996 | Jarvik | |
| 7,722,503 B1 | 5/2010 | Smith et al. | |
| 7,883,445 B2 | 2/2011 | Olrik et al. | |
| 7,942,320 B2 | 5/2011 | Joe | |
| 7,959,501 B2 | 6/2011 | Harmon et al. | |
| 7,959,540 B2 | 6/2011 | Jaquish et al. | |
| 7,981,000 B2 | 7/2011 | Watterson et al. | |
| 8,128,532 B2 | 3/2012 | Chen et al. | |
| 8,157,706 B2 | 4/2012 | Ainsworth et al. | |
| 8,172,724 B2 | 5/2012 | Solomon | |
| 2004/0162189 A1 | 8/2004 | Hickman | |
| 2004/0181129 A1 | 9/2004 | Glasgow | |
| 2005/0010426 A1* | 1/2005 | Chen ...................... G06Q 10/02 482/8 |

(Continued)

FOREIGN PATENT DOCUMENTS

WO          03/079134 A2      9/2003

*Primary Examiner* — Jay Liddle
*Assistant Examiner* — Alex F. R. P. Rada, II
(74) *Attorney, Agent, or Firm* — Kelly & Kelley, LLP

(57) ABSTRACT

A gym is provided having multiple, private booths for members to perform exercises. The member typically moves from booth to booth to perform different exercises. Preferably, an automatically generated workout program, based upon member input and fitness and test results, guides the member from booth to booth and provides a workout regimen that can be automatically changed from day to day, based on feedback, to accommodate the member's changing abilities.

20 Claims, 32 Drawing Sheets

(56) References Cited

U.S. PATENT DOCUMENTS

| | | | |
|---|---|---|---|
| 2005/0209887 A1* | 9/2005 | Pollner | G06Q 50/24 705/3 |
| 2006/0058156 A1* | 3/2006 | Cohen | A63B 24/00 482/4 |
| 2006/0189440 A1 | 8/2006 | Gravagne | |
| 2006/0223674 A1 | 10/2006 | Korkie | |
| 2007/0033068 A1 | 2/2007 | Rao et al. | |
| 2010/0042555 A1* | 2/2010 | Ranen | A63B 21/00 705/418 |
| 2011/0021954 A1 | 1/2011 | Nakano et al. | |
| 2011/0281687 A1 | 11/2011 | Gilley et al. | |
| 2012/0277891 A1 | 11/2012 | Aragones et al. | |
| 2013/0123068 A1 | 5/2013 | Sultan et al. | |
| 2013/0253943 A1 | 9/2013 | Lee et al. | |
| 2013/0274069 A1 | 10/2013 | Watterson et al. | |
| 2014/0081661 A1 | 3/2014 | Fu et al. | |
| 2015/0066170 A1 | 3/2015 | Harris et al. | |

* cited by examiner

|    | Exercise             | Type      |
|----|----------------------|-----------|
| 1  | Sumo squats          | Warmup    |
| 2  | Arm Rotations        | Warmup    |
| 3  | Low back stretch     | Warmup    |
| 4  | Lunge stretch        | Warmup    |
| 5  | Rotary stability     | Warmup    |
| 6  | Rest                 | Rest      |
| 7  | Vib Toe Touch        | Vibration |
| 8  | Overhead press       | Push      |
| 9  | Eagle ab             | Pull      |
| 10 | Eagle lateral raise  | Rotate    |
| 11 | Lunge stretch        | Full Body |
| 12 | Rest                 | Rest      |
| 13 | Vibration squats     | Vibration |
| 14 | Standing calf raise  | Push      |
| 15 | Ab crunch            | Pull      |
| 20 | Chest rotation       | Rotate    |
| 21 | Torso rotation       | Full body |
| 22 | Rest                 | Rest      |
| 23 | Vibration sumo squats| Vibration |
| 24 | Eagle calf           | Push      |
| 25 | Long row             | Pull      |
| 26 | Tricep press         | Rotate    |
| 27 | Vertical knee up     | Full body |
| 28 | Rest                 | Rest      |
| 30 | Vibration pushups    | Vibration |
| 31 | Back ext             | Push      |
| 32 | Ab crunch            | Pull      |
| 33 | Glute                | Rotate    |
| 34 | Squat pull           | Full body |
| 35 | Rest                 | Rest      |

FIG. 13

| Member Name | BOOTH #1 Start Time | BOOTH #2 Start Time | BOOTH #3 Start Time | BOOTH #4 Start Time | BOOTH #5 Start Time | BOOTH #6 Start Time |
|---|---|---|---|---|---|---|
| John | 09:00:00 | 09:01:20 | 09:02:40 | 09:04:00 | 09:05:20 | Rest/Review |
| Tom | 09:01:20 | 09:02:40 | 09:04:00 | 09:05:20 | 09:06:40 | Rest/Review |
| Jane | 09:02:40 | 09:04:00 | 09:04:00 | 09:06:40 | 09:08:00 | Rest/Review |

FIG. 20

EXERCISE FACILITY AND RELATED COMPUTER-GENERATED PERSONAL TRAINING SYSTEM AND METHOD

BACKGROUND OF THE INVENTION

The present invention generally relates to the field of health and fitness. More particularly, the present invention relates to an exercise facility wherein members can exercise privately. Moreover, the present invention relates to a method and system for providing a user with an automated personal exercise program which can be automatically varied according to the user's needs.

Today more than ever before, individuals are becoming more aware of their own physical fitness and the need to exercise. People follow exercise programs for a variety of reasons. These reasons include maintaining general well-being, assisting a weight loss program, increased muscular definition, and preparation for a particular sporting event.

Scientific evidence has established that exercise is known to improve and maximize individual health and to constrain the effects of aging. The proven benefits of fitness training often include, for example, increased muscle mass, lower resting heart rate, decreased cholesterol levels, lower blood pressure, and less stress on joints. To achieve these benefits, a consistent exercise program spanning an extended period of time is usually required.

In order to offer exercisers a complete and balanced program, exercise facilities typically include strength equipment that work targeted muscle groups as well as cardiovascular machines. New facilities or "gyms" are being opened nearly every day to provide a place where individuals can go to work out on various kinds of equipment and physical fitness devices. Modern exercise equipment is typically capable of adjustment to accommodate different fitness levels, i.e., a difficulty or resistance setting is usually provided that can increase or decrease the amount of exertion that it takes to operate the machine, thereby making it possible for a single machine to accommodate users over a wide range of ability levels. Gyms which include such exercise equipment are especially helpful and convenient for individuals who must sit at a desk and work during the day and get very little if any physical exercise, and for a relatively low monthly rate provides access to a fairly large number of exercise devices.

However, traditional gyms provide a limited number of stand-alone pieces of exercise equipment, or stations, on which to accomplish these exercises. Moreover, each device typically can only be used to perform a small set of specifically targeted exercises, for example, a triceps machine is operated by a user to exercise the user's triceps muscles, the target muscle.

The relative popularity of different types of machinery dictates the unique capacity of each machine. For example, men are usually far more likely to use a bench press than they are to use a leg abductor machine. Despite the numerous choices of exercise machines, it is a common occurrence to find increased demand for a certain type of equipment, wherein the demand is often larger than the capacity. Since the devices can only be in active use by one individual at a time, and each individual's exercise program is personal to that individual, there is often contention for pieces of exercise equipment between multiple individuals, resulting in bottlenecking or user downtime. Frequent bottlenecking during peak times is very disruptive to a workout program, often resulting in inefficient and time-consuming workouts. Many times an individual cannot achieve a regular workout and measure the individual's accomplishments because when the individual is ready to exercise with a certain type of equipment, that equipment is being used by another member of the gym. Frequently, if the next station or device is being used by someone else, a person will either cut short a workout session and/or skip one or more stations thereby precluding the achievement of a maximum benefit workout.

Although the multi-fold benefits of physical exercise are well established, most users are pressed for time and seek to maximize the benefit of such time as they have. Due to the increased demands on people's lives, exercisers are requiring more efficient use of their limited time at the gym. At the same time, gym operators typically have limited budgets and are not able to typically purchase more equipment to accommodate increased usage. Additionally, spending money on equipment for purchases requires more floor space into which to fit the additional equipment and increases the total maintenance cost for keeping all the equipment in working order.

Although the above-described problem of not having a particular station or exercise device available when the user desires occurs in some instances, in other instances users are simply overwhelmed with the large number of machines, stations, etc. Given the equipment that is available, the user can create a program from an almost limitless number of possible permutations. This can be overwhelming to those who are starting an exercise program using gym equipment for the first time. The uneducated user may not understand or appreciate the purpose of each of the machines or stations, and may not have a cohesive or effective exercise program. In such instances, the user may utilize only a few machines which they are comfortable with, without realizing the benefits of a fully integrated exercise program.

In the best case, an individual will work with a personal trainer in order to obtain the benefits of experience and customization of a workout for that particular individual. Personal trainers, coaches and the like often desire that the clients under their care and advisement follow a predetermined set of exercises to help the client improve in a desired area or to reach a particular fitness goal or just to prescribe a general fitness protocol or program. However, as might be expected, it can be difficult for a busy client to keep track of the trainer's recommended workout program and to track his or her own performance while following that plan. A strength program must be well planned in order to be effective. For example, a strength program may include exercises for every muscle group at resistance levels based on personal fitness levels. As fitness levels change, the resistance level should also be changed. Planning and tracking is typically a manual process. Workouts are manually recorded in log books by either the client or his or her trainer, in the event that the trainer accompanies and is present with the client during the exercise program.

However, using a personal trainer is expensive. Furthermore, while a personal trainer is useful in some cases, each trainer's knowledge varies and the end experience is random regarding achieving the preferred effects of a customized workout. Aside from monetary considerations by the user, some people are simply not interested in having someone else evaluate their personal performance and look over their shoulder and pressure them to increase their strength and fitness levels. In those instances when a personal trainer is periodically consulted with, the prescribed workout program given to the exerciser by the trainer may not fit the exerciser's ability on any given day. For example, if the exerciser has a cold, didn't get enough sleep the night before, etc., that exerciser may not have the strength or mental fortitude to accomplish the prescribed exercise program.

Of course, providing administrators, trainers, physiologists, and the like increase the gym owner's cost of operating the gym. However, in traditional gyms such individuals are typically necessary to meet the needs of at least some of the member users.

Another disadvantage of traditional gyms is the matter of privacy. The majority of gyms have both male and female users which belong to the gym and exercise there on a regular basis. This can create a level of discomfort in some individuals when working out. There is a wide disparity of muscular strength and fitness levels between these individuals. Some users feel as if they are being judged, looked upon critically, or even "checked out" while exercising. The public nature of gyms creates a fair degree of anxiety and self-consciousness in many members. In fact, many individuals who are interested in obtaining a workout at the facilities provided by a public gym are not willing to attend the gym due to these concerns. There has been a recent development in the opening of women-only gyms where only women are the patrons in order to overcome some of these concerns. However, these women-only gyms also cater to a wide range of women having different muscular strength, fitness levels, body types and the like so that only some of these concerns are alleviated.

Accordingly, there is a need for a new type of exercise facility which addresses the desire for users thereof to work out in privacy, obtain an effective full body workout in a reasonable amount of time, and have access to all necessary equipment during the workout or exercise regimen. The present invention fulfills these needs, and provides other related advantages.

SUMMARY OF THE INVENTION

The present invention is directed to a personal training system comprising a workout area configured to provide privacy to a user thereof. A computerized system generates a personalized exercise regimen for the user. At least one electronic device interfaces with the computerized system for directing the user to perform exercises within the workout area according to a predetermined exercise regimen sequence, which is generated by the computerized system for the user. User performance results are inputted into the computerized system for each exercise performed by the user. The computerized system automatically adjusts the user's exercise regimen according to the user's performance results input into the computerized system.

The workout area comprises at least one booth which is adapted for use by a single user at a time and which is configured to provide privacy to the user within the booth. Typically, the at least one booth comprises a plurality of booths, each booth being assigned an exercise.

The computerized system coordinates the sequence of the user's personalized exercise regimen with the exercises assigned to the plurality of booths. The at least one electronic device directs the user to move from one booth to another in a predetermined sequence in order complete the user's personalized exercise regimen. For example, each of the booths may be assigned a warmup or stretch exercise, a vibration exercise, a push exercise, a pull exercise, a rotate exercise, or a full body exercise. Exercise devices corresponding to the exercises to be performed by the user are disposed within at least a plurality of the booths for use by the user. Thus, as a user completes his or her workout regimen through the plurality of booths and leaves the last booth, other users within the booths advance, leaving the first booth open and available for a new user or member of the gym to enter into and begin his or her workout regimen. In exercise facilities where a plurality of sequences are provided, in other words multiple sets of booths are provided, such as three sets of booths each representing a sequence of exercises to be performed, as three users leave the last booth three users are able to enter into the first booth in the sequence of each set of booths in a very timely and organized manner.

A device may administer a reaction test to the user before exercising. The computerized system receives the user's reaction test results and adjusts the user's personalized exercise regimen according to predetermined reaction test result parameters. The at least one electronic device provides a time limit for the user to perform the exercise within the booth. The at least one electronic device comprises an electronic screen for displaying information relating to the exercise to be performed by the user. The electronic screen displays user identification, a tutorial for the exercise, and a performance goal for the user for the exercise, as well as a timer.

The at least one electronic device may comprise a touch screen display disposed within each booth. Alternatively, the at least one electronic device may comprise a personal electronic device having an electronic display screen and means for inputting data into the computerized system.

The exercise performance goal for the user comprises a goal number of repetitions of the exercise to be performed by the user within a predetermined time period. The exercise performance goal for the user typically further comprises a resistance or a weight to be used during the exercise by the user. The user performance results are input into the computerized system, such as using the electronic screen or personal electronic device.

In one form, the present invention comprises an exercise facility, such as a portion of an exercise facility or an entire exercise facility, comprising a plurality of booths. Each booth defines an enclosed space adapted to be used by a single user at a time and configured to provide privacy to the user while in the booth. Each booth has assigned thereto a predetermined exercise to be performed by the user within the booth. An exercise device is disposed within at least a plurality of the booths for performing the assigned exercise within that booth.

A computerized system is configured to generate a personalized exercise regimen for the user. The computerized system is configured to administer a reaction test to the user prior to exercising, and adjust the user's exercise regimen based on predetermined reaction test result parameters. The sequence of exercises to be performed by the user may comprise at least one stretch or warmup exercise, followed by a vibration exercise, push exercise, pull exercise, rotate exercise and full body exercise.

An electronic screen is within each booth for displaying information relating to the exercise to be performed within that booth. Means are also provided within each booth for inputting exercise performance results of the user into the computerized system. The booths include indicia, or are arranged in a sequence, in which the user is directed to move to perform different exercises corresponding to a sequence of exercises of a personalized exercise regimen to be performed by the user, which was generated by the computerized system.

The present invention is directed to a process for generating and performing a personalized exercise regimen. A personalized exercise regimen is automatically generated for a user by a computerized system. This includes entering user-related data into the computerized system. The user-related data includes physical attributes of the user, such as age, gender, height and weight entered into the computerized system. The user-related data also includes entering results of an initial fitness determination test performed by the user prior to exercising. The initial fitness determination test may comprise a grip strength test performed by the user. User desired fitness program, including a selection from a general fitness program, weight management program, strength enhancing program, muscle toning program, and a muscle endurance program, are also entered into the computerized system as user-related data.

A reaction test is performed by the user immediately prior to performing the sequences of exercises. The user's personalized exercise regimen is automatically adjusted, using the computerized system, based on the reaction test results.

The user is then directed to perform a sequence of exercises of the exercise regimen. Each exercise is assigned a time period to complete the exercise, and a number of repetitions of the exercise to be performed by the user. User exercise performance results are input for each exercise of the exercise regimen into the computerized system. The user's personalized exercise regimen is automatically adjusted by the computerized system based on the input user exercise performance results.

Typically, a plurality of booths are provided, each booth adapted for use by a single user at a time and each booth being configured to provide privacy to the user in the booth. Each booth is assigned an exercise to be performed in the user's exercise regimen. The user is directed from one booth to another in a predetermined sequence corresponding to the user's personalized exercise regimen and the exercises assigned to each booth.

Information relating to the user and the exercise to be performed within the booth according to the user's personalized exercise regimen is displayed on an electronic screen within the booth. The electronic screen may comprise a personal electronic device of the user having data relating to the booth assignment and user's personalized exercise regimen downloaded thereto. User exercise performance results are inputted into the computerized system immediately after each exercise using a data entry device within each booth.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 13 is a table depicting an exemplary workout regimen generated in accordance with the present invention;

FIG. 20 is a table illustrating exemplary start times and flow through booths for several users or members of the present invention;

DETAILED DESCRIPTION OF THE PREFERRED EMBODIMENTS

Figure 1:
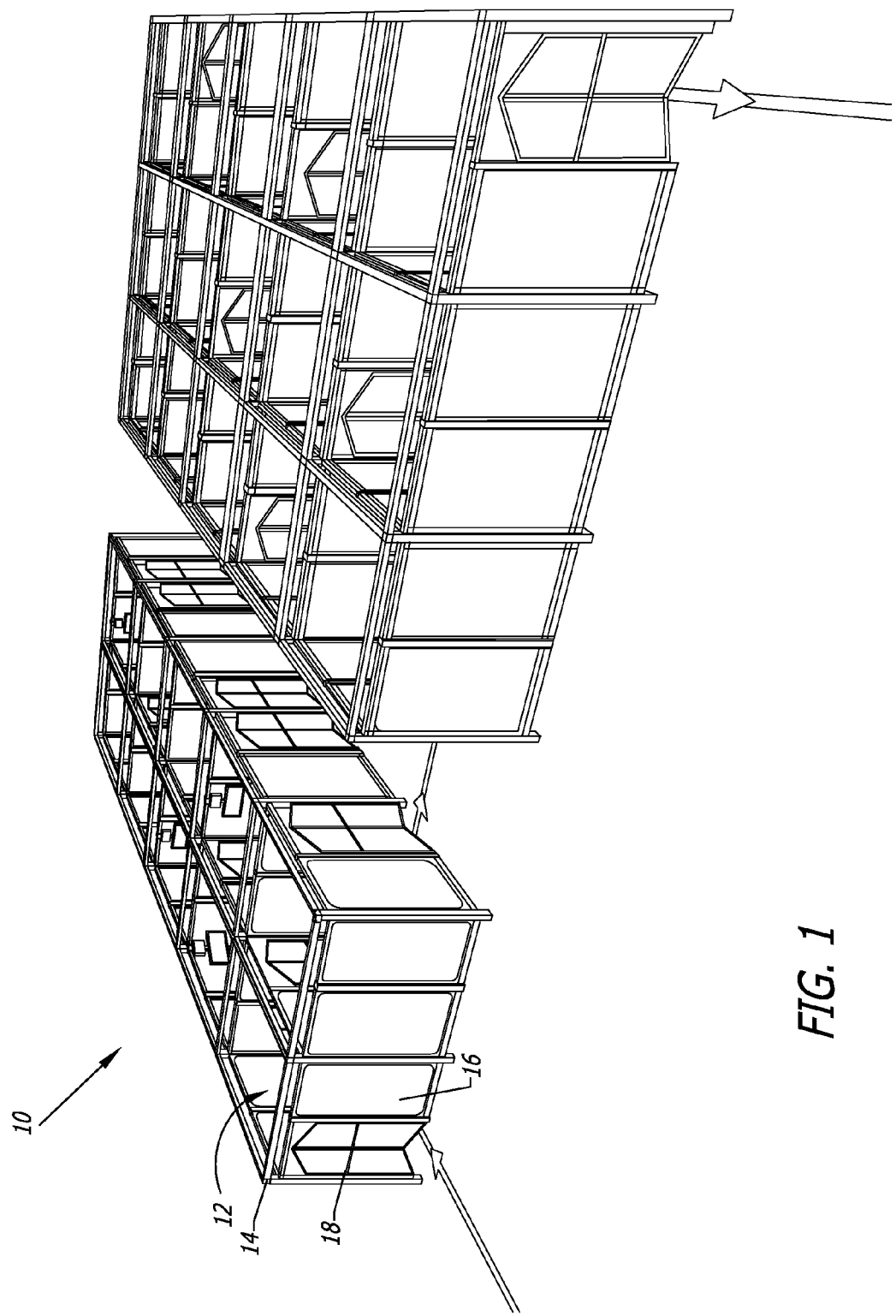
FIG. 1 is a perspective view of a plurality of booths of a workout area of an exercise facility, used in accordance with the present invention.

The present invention is directed to a public gym, sometimes referred to herein as exercise facility, design and arrangement, wherein each of the users (sometimes referred to herein as members, patrons, clients, individuals or exercisers) is able to perform their exercises in a private setting, so as to overcome the anxiety and self-consciousness of exercising in front of others. Each exercise is performed in a substantially enclosed area, referred to herein as a booth. It will be appreciated that the term "booth" represents a substantially concealed and private area which may comprise an individual room, which may be defined by walls, dividers, curtains, etc. which provide the exercise anonymity and privacy while performing the exercise.

In a particularly preferred embodiment, an exercise device, such as a piece of exercise equipment or machinery, exercise mats, exercise devices, etc. as needed is placed in each booth, such that the user moves from one booth to another in order to perform a different exercise in each booth using different exercise machines, devices, etc. Typically, the user is provided an individually personalized exercise program, such that the user moves from one booth to another in order to perform different exercises at a level of repetitions and resistance specific to that user, as described more fully below.

The present invention incorporates a comprehensive, personalized exercise program for individuals that want to be directed by professionals, while maintaining the privacy they desire without having to spend additional funds for a personal trainer. A user who wishes to achieve personal fitness or improve upon sports-related skills is offered a workout program, which is automatically generated by a computer system according to algorithms, data input, and the facilities to achieve their goals within a defined period of time. The workout programs are based on established sports physiology and personal fitness procedures and can be tailor-made to suit the requirements and criteria of each individual.

The method and system of the present invention provides users a workout that is unique to the fitness industry in that it is more efficient, user-specific, and cost-effective than traditional training methods.

The method and system of the present invention reduces the need to maintain multiple administrators, trainers and physiotherapists. Instead, the system of the present invention provides an automated solution which can provide a decision-based system that guides the users based on the goals they have set, their profile and medical history, as well as results of a fitness test, reaction test, and results from prior workouts.

The present invention also reduces the manual bookkeeping in terms of both managing the gym facility, memberships, fees, equipment, workout programs, registration and slot booking for training. The present invention utilizes interactive tools such as kiosks, display screens, mobile applications and/or network access to the users to facilitate registration, slot booking and obtaining updates of their achievement from the program.

In order to accomplish these objectives, the present invention provides each patron or user an individualized exercise program, preferably of specifically sequenced exercises and rest periods, tailor-made to that individual user and adaptable from workout session to workout session. The present invention provides an automated directed workout which guides the user from one exercise to another in a timed fashion, so as to complete a full exercise regimen within an allotted time period. In a particularly preferred embodiment of the present invention, the user performs these exercises in a private setting and receives guidance and is able to provide input via technology incorporated into the system.

With reference now to FIGS. 1-12, the present invention is directed to a gym or exercise facility 10 having a workout area which is adapted for use by a single user or gym member at a time and which is configured to provide privacy to the user within the booth 12. Typically, as illustrated in FIG. 1, the workout area comprises a plurality of booths 12 such that users, usually members or clients of the gym 10, can exercise privately and anonymously within each booth 12. The booth, for the purposes herein, means any room, divided area, pod, etc. which provides a sufficient degree of privacy and anonymity and space for the member to perform his or her exercise therein. Each booth 12 is assigned an exercise to be performed by a single user or member at a time within the booth 12. Typically, a single exercise device or piece of equipment will be disposed within each booth 12, such that a single member performs an exercise using that device or equipment. It will also be appreciated that the booth 12 can include an exercise mat or the like, for performing an exercise or stretching which does not require an exercise device. The exercise to be performed within the booth 12 and/or the exercise device or piece of exercise equipment can be changed over time in order to accommodate the needs of the invention.

Thus, as illustrated in FIG. 1, a single room or workout area of a gym is subdivided into a plurality of different and distinct booths 12. Typically, the booths 12 are present within a single room or area of a gym, although it is contemplated by the invention that the booths 12 may fill a portion of a gym structure, the entire gym structure, be placed on more than one level or floor of the gym, or may be divided and in distinct areas of the gym.

With continuing reference to FIG. 1, in a typical embodiment, each booth 12 is formed by a framework 14 which supports a plurality of panels 16, which serve as dividing walls. The dividing walls or panels 16 can be comprised of any suitable material, but are typically semi-transparent or opaque so as to provide privacy and anonymity to the member exercising within that booth 12. Moreover, the panels 16 are of a sufficient height so as to provide privacy and anonymity to the member exercising within the booth 12. Such panels or dividers 16 can be of a predetermined height, such as five to seven feet in height, or extend from the floor to the ceiling, as is deemed desirable or necessary. Typically, however, the dividing panels 16 do not extend to the ceiling, but instead are of a sufficient height so as to provide privacy to the member while being able to be sufficiently lit from lighting fixtures placed in the ceiling of the gym, which also provides sufficient air flow throughout the plurality of booths 12.

Figure 2:
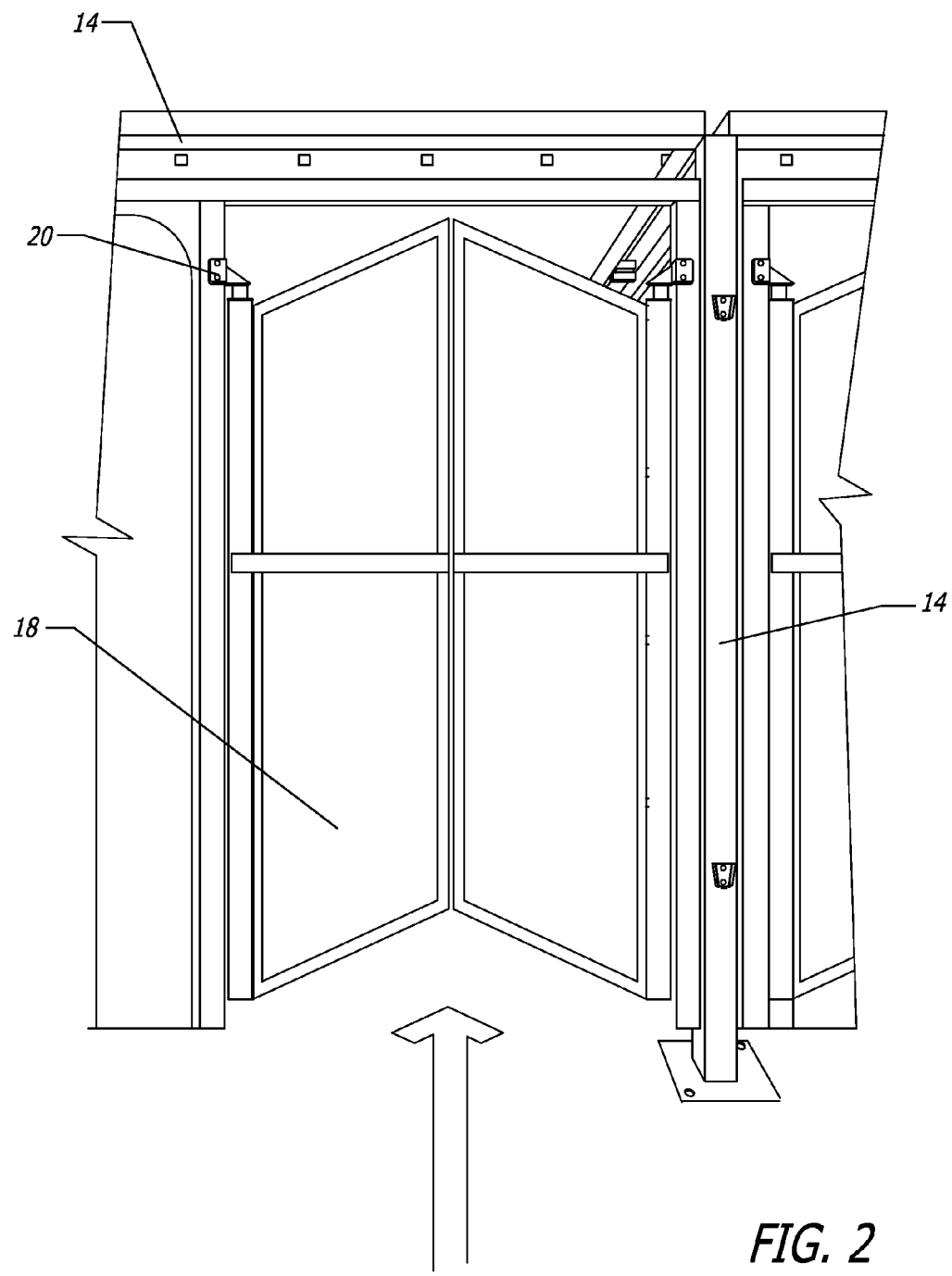
FIG. 2 is a front elevational view of an entrance to a booth.

With reference again to FIG. 1, each booth 12 has at least one door 18 for entry and exit. Each booth 12 may have an entry door 18 as well as an exit door 18, which leads to another adjacent booth, as illustrated. FIG. 2 illustrates an exemplary door 18 supported by vertical and horizontal framework members 14. The door 18 may include spring biased members 20 such that the door 18, upon being opened, will automatically close behind the individual entering or exiting from the booth 12. In a particularly preferred embodiment, the booths 12 share dividing walls or panels 16 so as to be immediately adjacent to one another, and so that entry and exit doors 18 are shared between at least a plurality of the booths 12, such that a user or member moves from one adjacent booth 12 to another in a predetermined pathway, as will be more fully explained herein. However, it will also be appreciated that the booths 12 may comprise distinct enclosed areas having their own entry and exit, depending upon the configuration and need of the gym or exercise facility.

Figure 3:
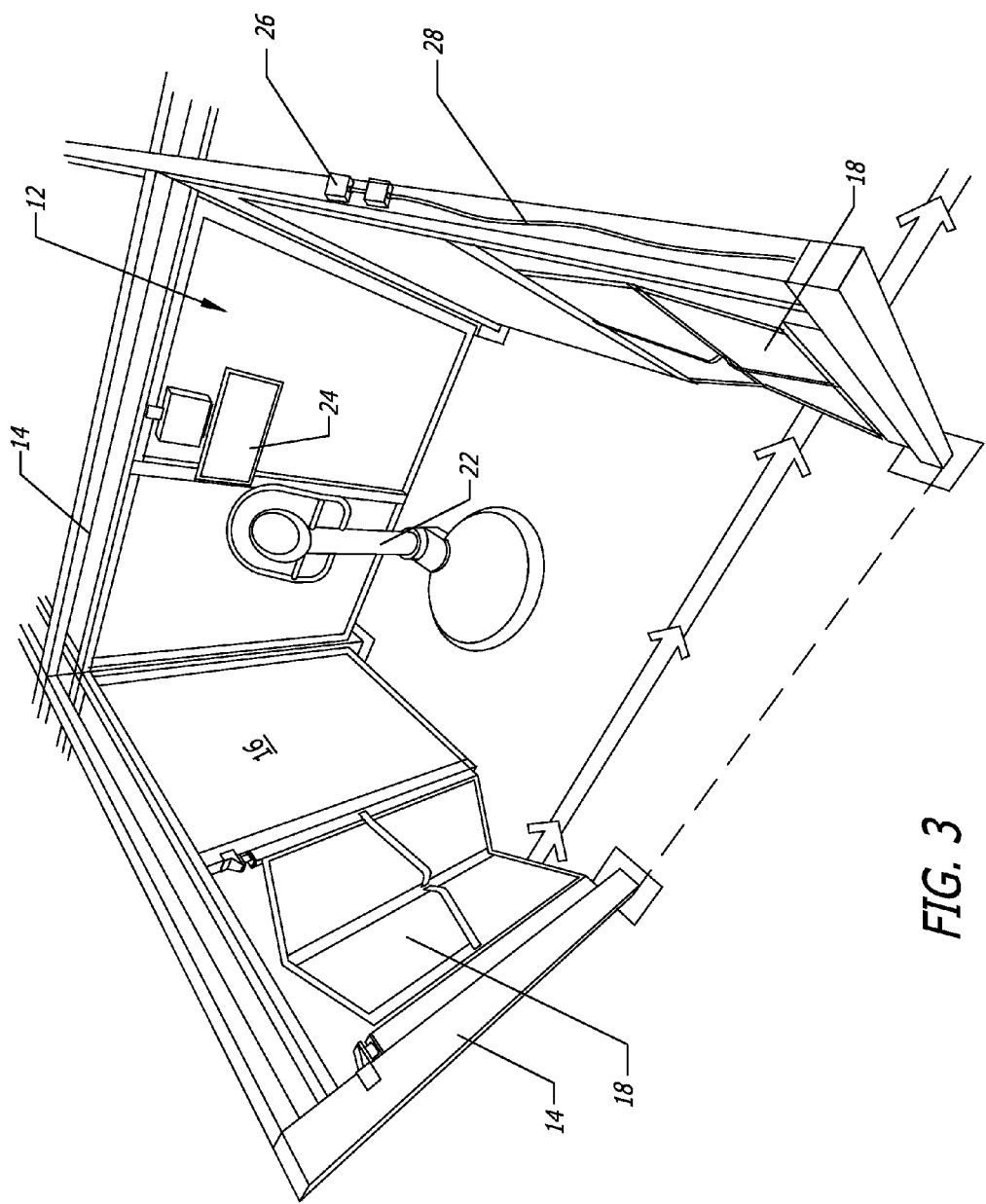
FIG. 3 is a perspective view of a booth, having a wall removed therefrom for purposes of illustration, illustrating an entry, an exit, an exercise device and a display screen, in accordance with the present invention.

With reference now to FIG. 3, a booth 12 is illustrated with a side wall thereof removed for viewing purposes. It will be seen that the wall panels 16 substantially encompass the booth 12, typically enclosing four sides of the booth 12 so as to make an enclosed room or booth. Doors 18 provide entry and exit points from the booth 12. The panels 16 and doors 18 are mounted on vertical and horizontal framework members 14. As mentioned above, typically each booth 12 includes a single exercise device or piece of machinery 22. In this manner, typically, each booth 12 is used by a single member for a single exercise utilizing the exercise device or machinery 22 at any given time. The booths 12 are of a sufficient size so as to accommodate the user, the exercise to be performed, and any exercise device or piece of machinery 22 therein to perform the exercise. As such, the booth may be as small as fifteen square feet or as large as two hundred square feet, but more typically between twenty-five and one hundred square feet in size so as to comfortably accommodate the user, any exercise device and the exercise to be performed while still permitting the gym or exercise facility to provide a sufficient number of booths so as to accommodate a sequence of exercises to be performed by the users and gym members in accordance with the personal training system and method utilizing the booths in accordance with the invention.

It is believed that the use of individual booths 12 will eliminate distractions which will allow for better concentration and a more effective workout. The privacy and anonymity provided to the member from each booth 12 also eliminates the intimidation or "judge your neighbor" factors which many public gym users dislike, or even are dissuaded from utilizing a public gym for these reasons. Of course, this will take away much stress and anxiety from these individuals working out in a private individual booth 12 setting at each workout station.

Each booth 12 may include at least one electronic device, such as the illustrated display monitor 24 therein. The display monitor 24 could be used to watch television, movies, etc. while exercising within the booth 12. This would be the case, for example, if the exercise device 22 within the booth 12 were to be used for a prolonged period of time, such as twenty minutes or more. Such exercise device 22 could comprise cardio machinery, in the form of exercise bikes, treadmills, and the like. In this manner, the member could view television, movies or other such media while performing the prolonged exercise.

However, typically the display monitor 24 is used as an instructional tool to provide the member with a tutorial and guidance on how to perform exercises within the booth 12, such as how to properly utilize the exercise device 22 or perform the desired exercise. As will be more fully described herein, in a particularly preferred embodiment, a computer implemented, individualized workout regimen is provided to each member and the display screen 24 is used to effectuate this system.

Figure 10:
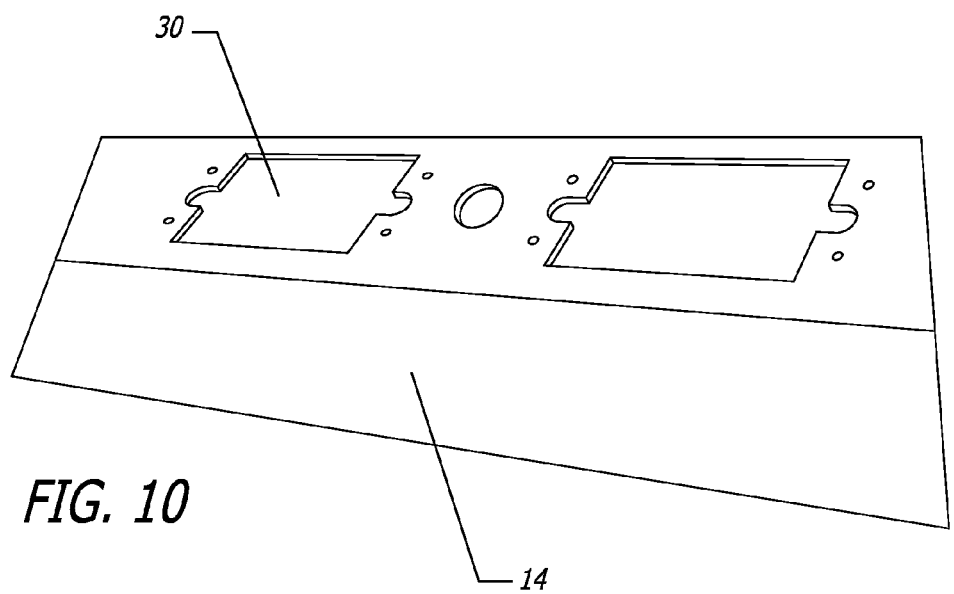
FIG. 10 is a fragmented perspective view of electrical outlet cutouts of a frame of the booth, used in accordance with the present invention.
Figure 11:
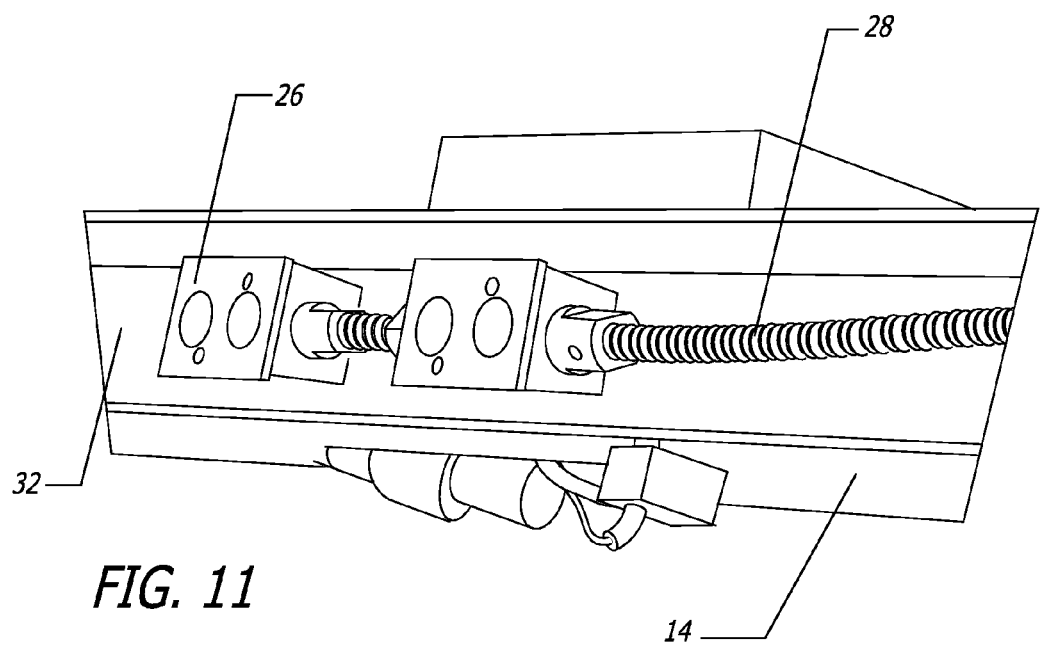
FIG. 11 is a perspective view of electrical wiring and outlets disposed within the frame of the booth, in accordance with the present invention.
Figure 12:
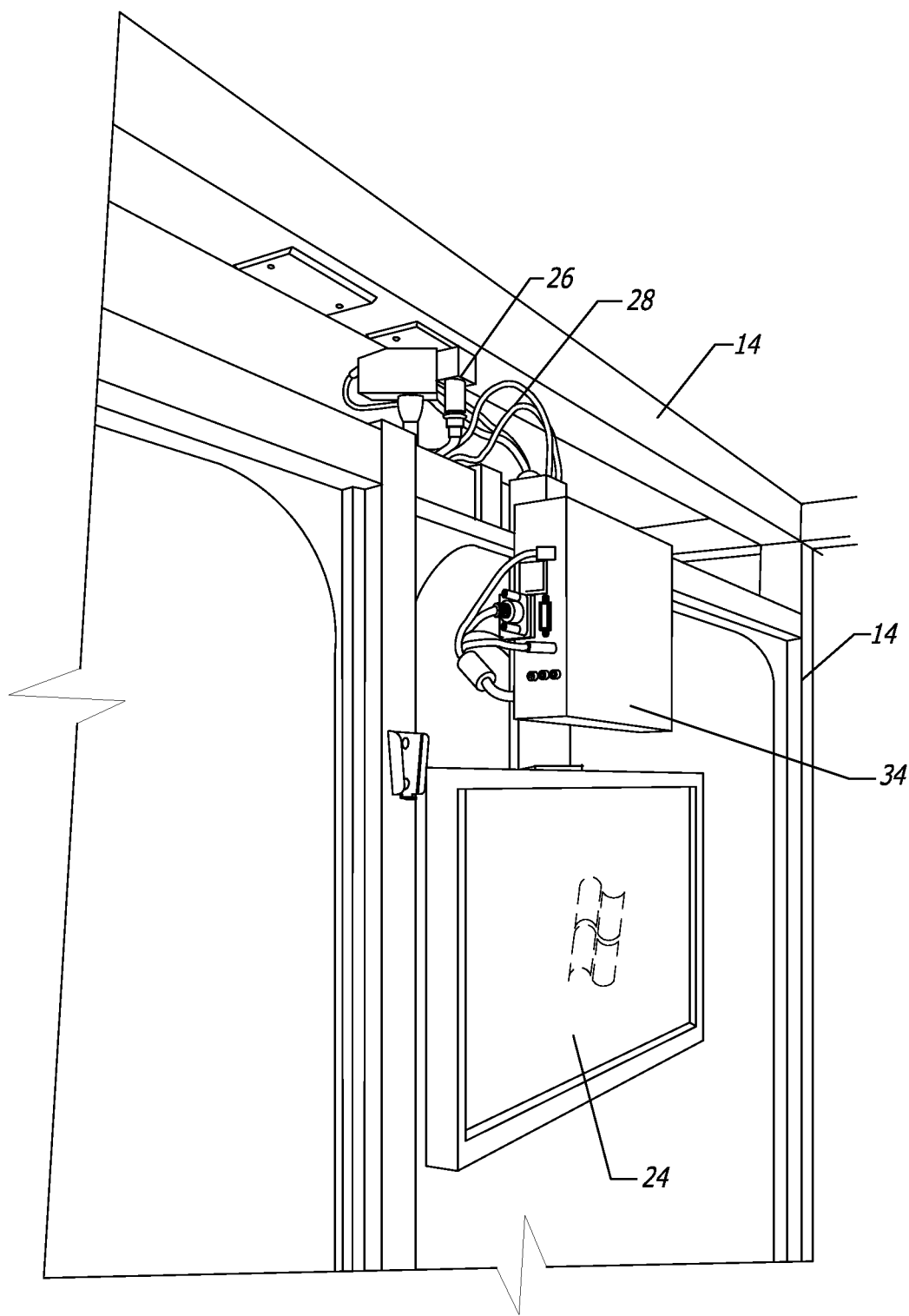
FIG. 12 is a perspective view of an electronic device in the form of a display screen and computer within a booth, in accordance with the present invention.

As such, the workout area of the exercise facility or gym includes the necessary electrical outlets and plugs 26 and wiring 28 to provide the necessary electricity, cable and/or Internet cabling and access, etc. Preferably, the frame members 14 are able to accommodate such electrical outlets 26 and wiring 28, such as being channeled or the like. For example, as illustrated in FIGS. 10 and 11, framework members 14 may include pre-punched holes 30 for the insertion and coupling of electrical outlets 26, as needed. FIG. 11 illustrates such electrical outlets 26 disposed within or otherwise coupled to such cutout openings 30 and disposed within a channel 32 of the framework 14. FIG. 12 illustrates a display screen 24, operably coupled to a receiver and/or computer unit 34 for receiving visual and audio media to be displayed on the screen 24, access to a network and server computers, downloading of media, individualized workout regimens, etc.

With reference now to FIGS. 4-8, it may be desirable to periodically replace one piece of exercise equipment with another within a given booth 12. This may be due to the previous exercise device or piece of machinery malfunctioning, becoming aged and obsolete, or to alter the exercise provided within that booth. Due to the enclosed nature of the booths, means are necessary in order to easily and selectively remove one or more panels in order to provide access to the internal contents of the booth, such as the exercise device 22 therein.

Figures 4, 5, 6A, 6B:
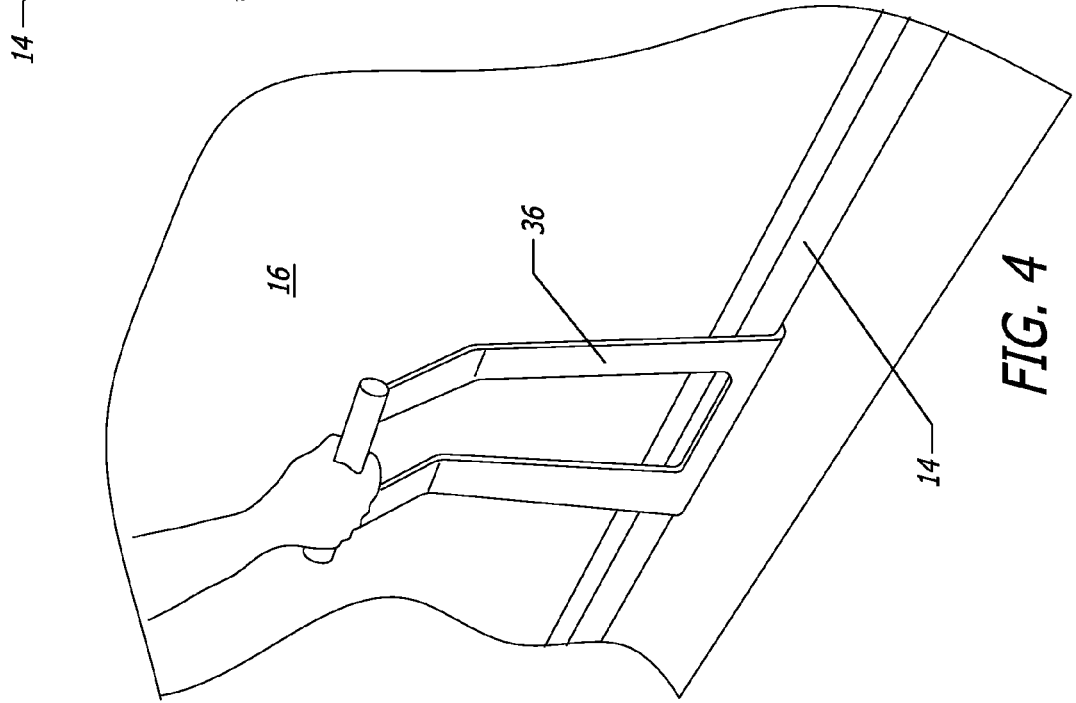
FIG. 4 is a fragmented perspective view of a tool used for placing or removing walls of the booths.
FIG. 5 is a side diagrammatic view illustrating interconnection of locking members of booth members.
FIGS. 6*a* and 6*b* are male and female interconnecting members, respectively, used in accordance with the present invention.
Figure 7:
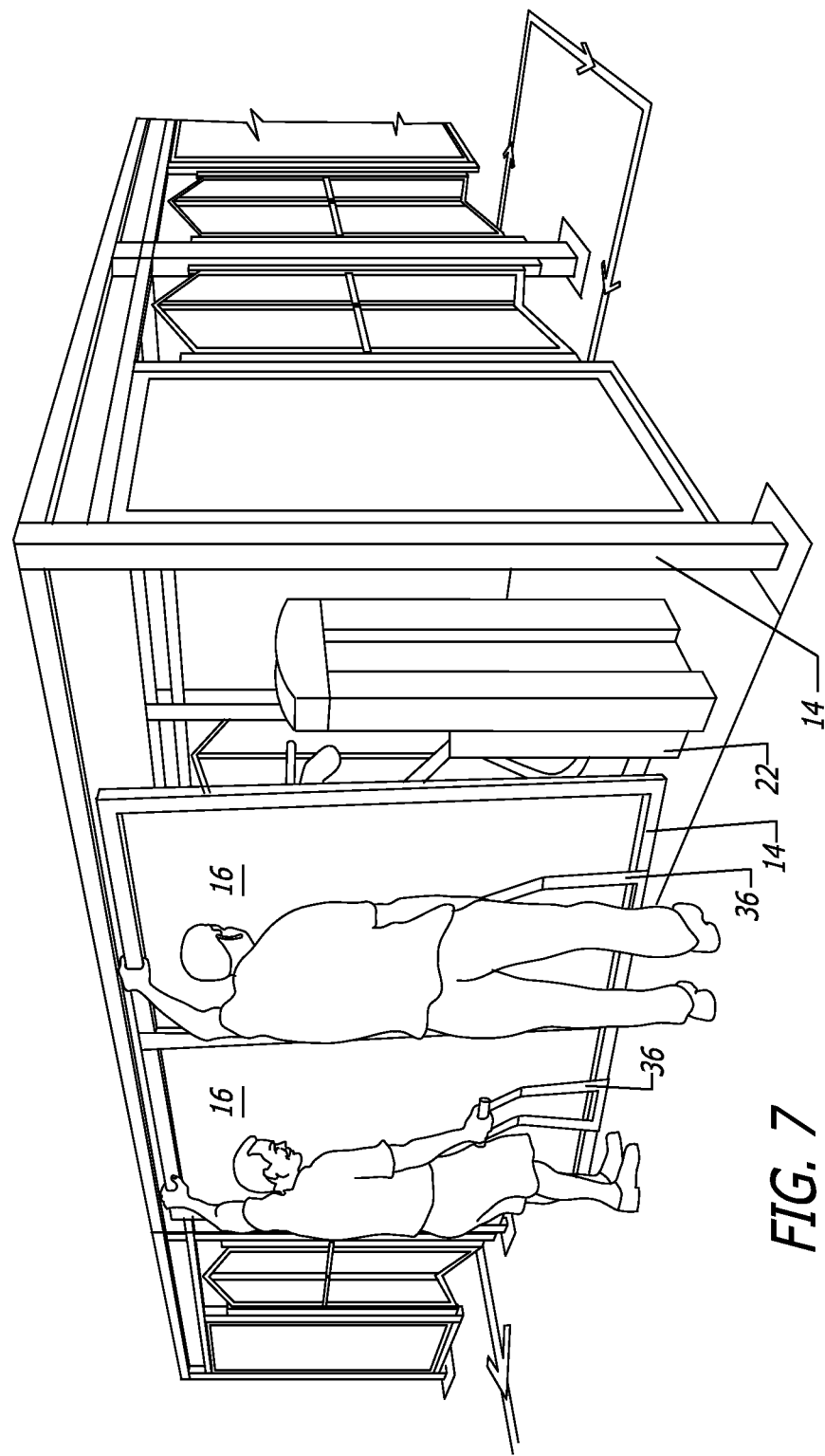
FIG. 7 is a perspective view illustrating the movement of a wall of a booth, in accordance with the present invention.

FIG. 4 illustrates a manual lifter tool 36 which can be disposed below a lower edge of the bottom framework 14 so as to lift the panel 16, as illustrated in FIG. 7. This can be done with one or two individuals, as illustrated. The framework 14 of the panels 16, and adjacent framework which is not bolted or otherwise secured to one another, include releasable locking elements 38 and 40, which can serve to lock a panel to an adjacent typically vertical framework 14.

Figure 8:
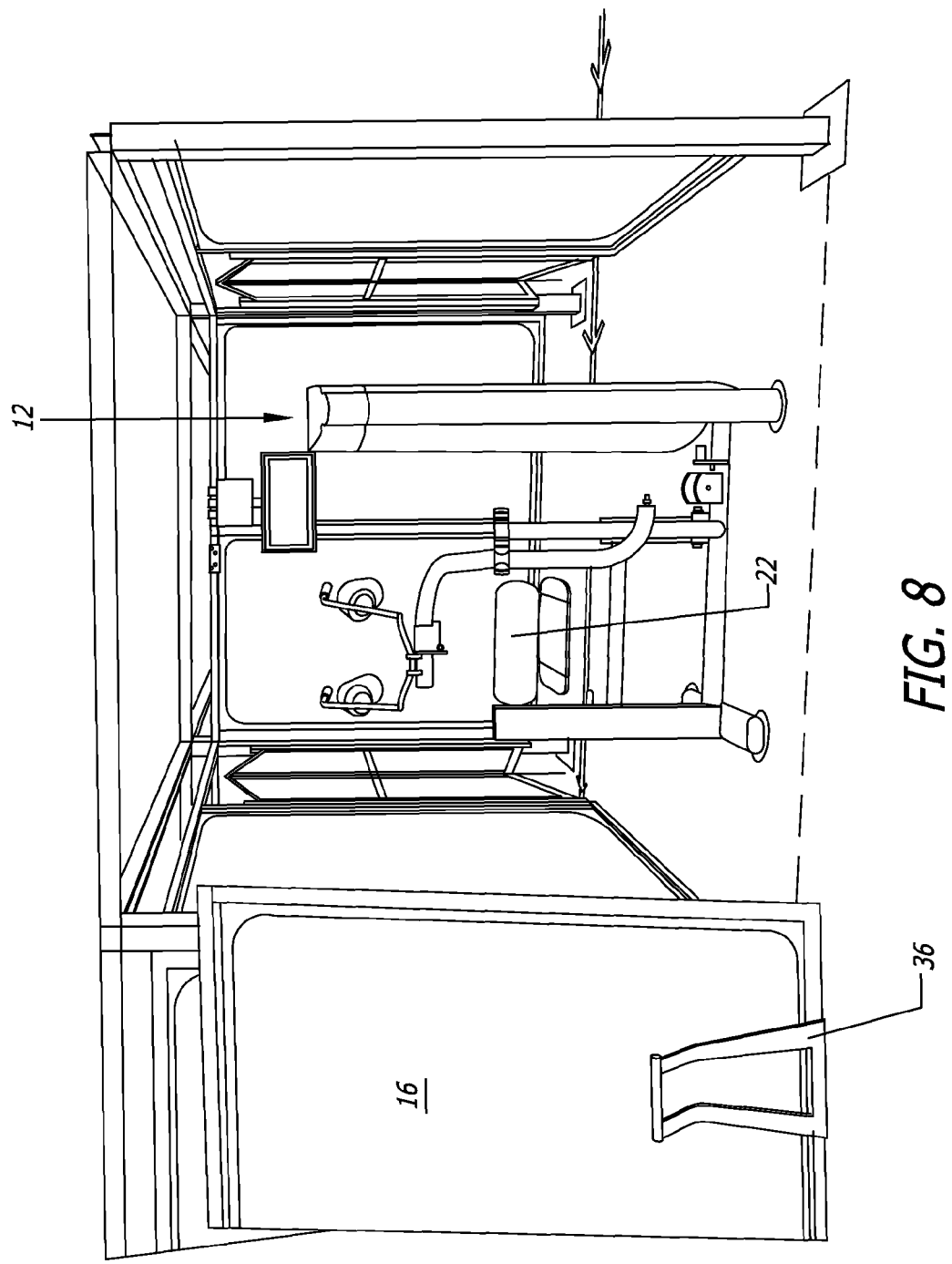
FIG. 8 is a front elevational view of a booth having a wall removed therefrom and used in accordance with the present invention.

FIGS. 6a and 6b illustrate a male locking element 38 and a female locking element 40 which can be slidably engaged with one another so as to lock adjacent panels and/or frame members 14 to one another. As illustrated in FIG. 5, the male locking element 38 is slid into the receiving portion of the female locking element 40. This can be done, for example, by dropping the male locking element 38 into the receiving female locking element 40, which has wings 42 defining gaps or grooves into which the edges 44 of the male locking element 38 slide into. In order to remove the male locking element 38 from the female locking element 40, and thus the framework or panel attached to the male locking element 38 from the panel or framework attached to the female locking element, the panel or framework having one or more male locking element(s) 38 attached thereto is merely lifted with respect to the other framework or panel having the female locking elements 40, as illustrated in FIGS. 4 and 7. This enables the one or more panels 16 to be removed and set to the side while the interior of the booth 12 is accessed, so as to replace, for example, an exercise device 22 therein, as illustrated in FIG. 8.

Figure 9:
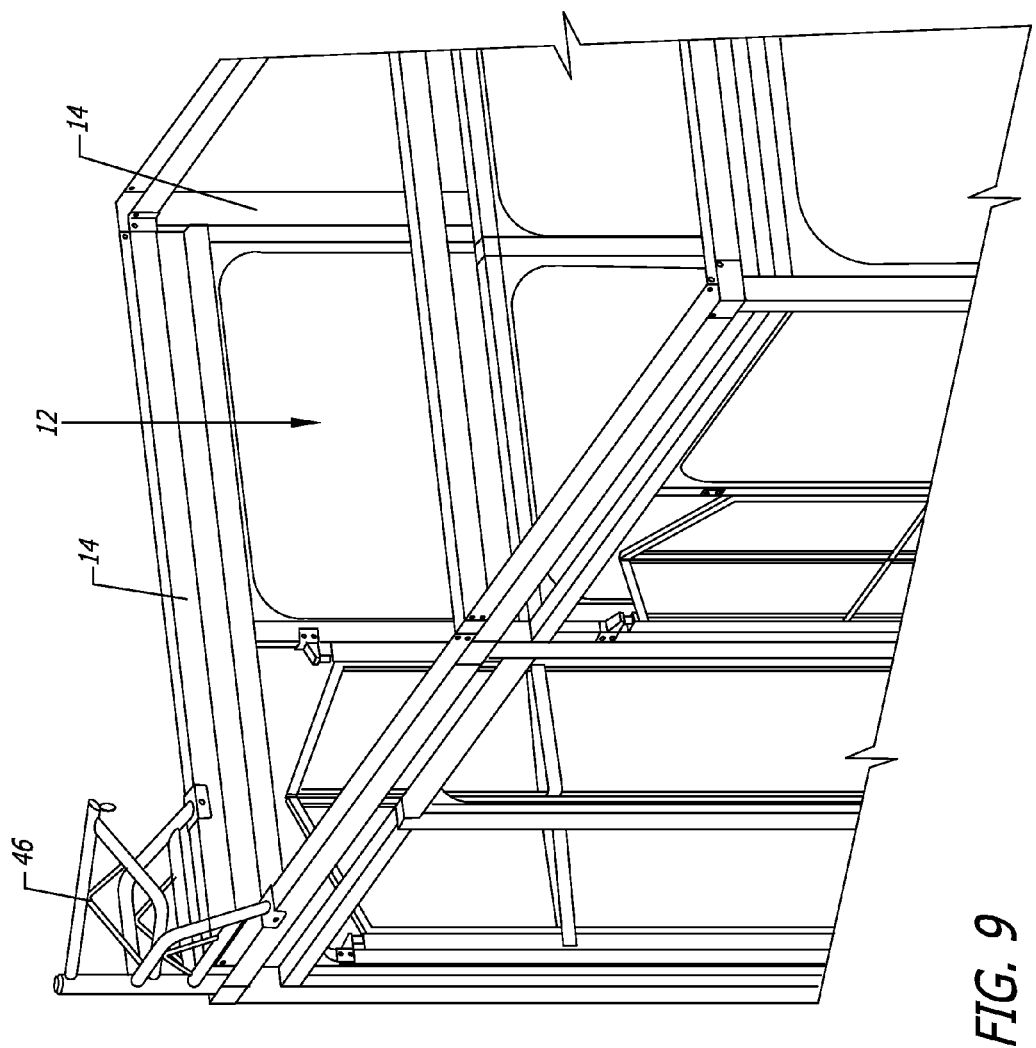
FIG. 9 is a perspective view of an exercise device attached to upper framework of a booth, in accordance with the present invention.

With reference now to FIG. 9, it is contemplated by the present invention that instead of a piece of exercise machinery within the booth 12, an exercise device 46, such as that illustrated in FIG. 9, may be attached to the framework 14 in order to perform the exercise. This can be, for example, a device having a cable and pulley system for performing lat pull downs, triceps pull downs, or the like. Other such devices, such as a pull-up bar, are also contemplated.

It will be appreciated that the size of each booth 12 can be uniform, or adjusted in order to accommodate the space requirements for the exercise for that booth 12. For example, a booth 12 having a relatively large piece of exercise equipment can be made with varying size panels or multiple panels in order to accommodate the piece of exercise equipment, or a booth 12 in which a lat or triceps pull down device 46, as illustrated in FIG. 9 or having simply a stretch or sit-up mat will require less space or fewer panels and thus be smaller in size. The interlocking framework 14 of the male and female locking members 38 and 40, and bolts, nuts, or other fastener systems can be used in order to create the desired number of booths 12 and adjust the size of the booths as needed. Typically, the booths 12 are placed adjacent to one another and provide passageway from one to another, as illustrated herein.

It is also contemplated by the present invention that the environment in each booth 12 can be altered to enhance the exercise experience. For example, the booths may have a certain type or degree of lighting which will be conducive to the user. The air can be conditioned to a desired temperature, humidity, or even desirable smells can be placed into the circulated air of each booth. The color scheme and/or design of each booth can also be altered to enhance the user's experience. It is also contemplated by the present invention that speakers could be used to play music for the individual, and the member user could select from different genres of music or a playlist to be played as a user moves from one booth 12 to another. Of course, the member could also plug in a personal hand-held electronic device to play the member's music within each booth 12 as well.

It is contemplated by the present invention that the display monitor 24 be interactive, such as comprising a touch screen monitor. Of course, keyboards, a mouse, or other interactivity means could be incorporated such that the user can interact with the display screen and input data as needed. This could comprise selecting television channels, music, etc. In a particularly preferred embodiment, this interactivity is used for purposes of the individual's personalized exercise regimen and program.

Although the gym could be configured such that each member performs an exercise within a given booth 12 and then finds another booth having a desired piece of exercise equipment therein to perform their own exercise regimen or one created by their own personal trainer, in a particularly preferred embodiment an exercise regimen with a predetermined exercise sequence is provided to the member. This entails the member typically moving from one booth to another booth to perform a particular exercise within that booth, such as performing an exercise utilizing an exercise device or machine 22 within that booth. This further facilitates the member's experience at the gym by means of the member being directed from booth to booth to perform different exercises in accordance with an assigned exercise program such that the member does not need to concern himself or herself with the exercises to be performed that day or to find a booth or piece of exercise equipment which is available at any given time.

In accordance with the present invention, an exercise workout regimen is provided to each member of the gym which is specifically personalized and tailored for that individual, yet consisting of the exercises to be performed in the various booths of the gym. Preferably, each workout session will exercise and strengthen all of the major muscle groups of the body of the members. Upon providing information and test results, a personalized workout regimen is provided to each member of the gym which is generated by a computer program of a computerized system.

Each member of the gym, as will be more fully described herein, will schedule a specific session at the gym and begin at an assigned booth number. Each booth will be assigned a particular stretch, warmup, exercise or rest period. The individual will proceed from booth to booth, as directed by the computerized system, thus obtaining an optimum workout without having to worry about which exercise to perform next, what the individual's performance results were for that exercise in a previous workout session, or how much additional weight or how many additional reps should be done by that individual for that exercise. The computerized system has algorithms which tracks the input, typically merely the entry of the number of repetitions, by the member from exercise to exercise and workout session to workout session and automatically alters the workout regimen for that individual. Thus, for example, if the computer program, based upon prior entered information, determines or predicts that the individual should be performing ten repetitions of twenty pounds, but that individual can in fact perform twenty-five repetitions, the computer program will adjust the workout regimen for the individual at the next workout session such that either additional weight and/or additional repetitions will be part of the exercise regimen for that individual.

This happens behind the scenes as the gym member merely enters the assigned booth and is instructed by the system, such as via the touch screen display, the exercise to be performed, the weight or resistance to be used, the goal number of repetitions, and the time in which to perform the exercises. The system will prompt the member at the end of the allotted time to input the number of repetitions performed. The system will then prompt the member to move to the next booth for the next exercise, or possibly a rest period.

The present invention contemplates a full body exercise by varying the exercises to be performed with arm muscle groups, chest and back muscle groups, core muscle groups, and leg muscle groups. Cardiovascular exercises are also contemplated by the invention. By varying the type and number of exercises, a full body workout can be obtained in a relatively short period of time, such as within thirty minutes.

It is also within the scope of the present invention that a series of booths be specialized so as to create a cardiovascular workout, an upper body workout, a lower body workout, etc. to provide the gym member the flexibility in choosing to focus on these types of exercises. This would entail having multiple series or sequences of booths which are independent of one another. For example, three sets of thirty booths could comprise three sequences, each sequence providing approximately a thirty minute workout. Exemplary exercise programs which can be created by sets of booths and selected by the user or gym member include a general fitness program, a weight management program, a strength enhancing program, a muscle toning program, and a muscle endurance program. A particular set of booths may have exercise equipment or exercises assigned thereto which are more specific or applicable to a given desired fitness program. Alternatively, or in addition to, the automatically generated workout regimen created by the computerized system could account for the desired and selected fitness program so as to alter the weight or resistance, number or repetitions or the like of each exercise to be performed. For example, the number of repetitions at a given weight may be increased for a muscle endurance program, whereas the amount of resistance or weight would be increased for a strength enhancing program of a given exercise.

In a particularly preferred embodiment, in order to automatically generate a workout regimen for a member of the gym or exercise facility, the general fitness level of the member is determined. Currently, more experienced and more educated personal fitness trainers have the member max out on every single piece of exercise equipment which the personal trainer plans on using in a workout program for the user. As will be imagined, this takes a significant amount of time and data entry. Personal trainers which are not as skilled or educated, simply set up a workout program of a certain number of repetitions at a certain resistance or weight without any idea of what the individual is capable of, and then adjusts the workout program if the individual either can't perform the number of repetitions at that weight or if the number of repetitions and/or weight is too easy for the individual.

However, in accordance with an embodiment of the invention, the user takes a single fitness test. In a particularly preferred embodiment, this comprises a strength test, such as a grip strength test using a hand dynamometer. This determines the strength of the individual, and it has been found that there is a strong correlation between this test and total body strength. Although the use of a grip strength test is particularly preferred, it will be appreciated by those skilled in the art that other fitness tests or strength tests can be used in its place. The strength test replaces the need to do a maximum test on every single piece of exercise equipment in order to calculate how much weight or resistance should be used in those exercises by the user. The computerized system of the present invention utilizes algorithms associated with the fitness strength test so as to calculate a baseline fitness and strength level of the member without having to do so many tests. Moreover, the results of the strength test set a baseline of weight and repetitions for that individual for each particular exercise to be performed.

In accordance with the present invention, a patron or member of a gym incorporating the system of the present invention, or, in other words a user of the method and system of the present invention, also completes a health history and physical trait questionnaire. The user may provide user-related information including the user's age, gender, weight, height, physical limitations or other health concerns, and the like. This may be done online or when the user first attends the gym incorporating the present invention.

As part of the registration and data entry process, the user takes a fitness test, such as the above-described grip strength test. The user may indicate a desire to attain general fitness, weight management, strength, or muscular endurance or toning, etc. Based upon this desired fitness program selection, the data entered in the health history questionnaire and the strength test results, the computerized system of the present invention generates, in an automated fashion, a workout program for that individual which takes into account all of these factors so as to be personalized and individualized for that particular individual user. This automated analysis is based upon physiological exercise science which is customized for the individual in order to maximize the results the individual is seeking to attain. The computerized system utilizes an algorithm to determine appropriate resistance or weight and repetitions for the individual to use for the various exercises according to a generated workout regimen.

For example, a young six foot two inch, two hundred twenty pound male having high strength and no health history concerns interested in improving his strength will be given a different workout regimen than another male who weighs three hundred pounds and is interested in weight management, or a five foot three inch, one hundred pound female of advanced age who is interested in general fitness. The computerized system of the present invention can take into account the factors of all three of these individuals and create a unique workout program for each one of them. This can be accomplished even if the equipment or workout stations are the same and the time interval of exercising at each station is the same.

Once the initial workout regimen is generated by the computerized system after the registration process and fitness test, a reaction test may be used to determine the amount of fatigue and mental clarity that the individual is experiencing on any particular day. It has been found that individuals have variations from day to day as to their ability to complete a workout regimen. For example, the individual might be tired due to lack of sleep, illness, etc. which can adversely affect the individual's ability to complete the workout regimen. The present invention may take such variations into account by having the individual perform a reaction test before the workout regimen is started. The results of the reaction test will give an indication of the mental and physical alertness and well-being of the individual that particular day, and the algorithms of the present invention will adjust the weight or resistance and/or the number of repetitions to be performed for the exercises of the workout regimen that day based on predetermined reaction test result parameters. The reaction test can be as simple as selecting a sequence of lights presented on a touch screen display, and measuring the reaction time between the lighting of the object and the member pressing the object. The reaction test may be performed multiple times, and the user's reaction times averaged.

In accordance with the present invention, in addition to the automated generation of an individualized workout program for each individual user, the system of the present invention also analyses feedback provided by the user during the exercise program and may take into account the degree of exercise readiness of each individual at the beginning of each workout session and also in order to alter and customize the workout program for the user in the future.

Typically, each day that the user comes to exercise, he or she takes a reaction test before that workout. Based upon the results of that test, the workout regimen or program for that day may be altered to match the level of fatigue or mental clarity of the individual, as determined by that individual's reaction time or ability. This may be done, for example, by timing the individual's performance in selecting a sequence of lights, shapes, etc. utilizing an electronic display or other electronic data entry method. It has been found that if the individual is fatigued, such as due to lack of sleep or sickness, the reaction test results will differ compared to when the individual has had sufficient sleep and is healthy. If the individual is fatigued, the computerized system of the present invention will automatically alter the workout program for the user for that particular day in order to take into account the fatigue. The reaction test gives the system a measure of the neurological readiness of the individual that day. Individuals who are ready for a higher amount of stress will be given a higher stress, but those who need a break that day will be given a lighter workout program, such as fewer repetitions or lighter weight or less resistance. The reaction test essentially taps into the nervous system of the individual and helps the system determine how prepared the individual is that day for his or her workout.

The workout program consists of a given number of exercises performed over a given period of time. These exercises typically involve a piece of exercise equipment or machine but can involve a manual exercise, such as sit-ups, push-ups or the like. The system of the present invention automatically generates the workout program for that individual on that particular day based upon the aforementioned tests and the number of repetitions entered into the system at each exercise station by the user. Each exercise is timed and the user provides data input as to the progress made during each exercise, such as entering the number of repetitions of the exercise performed. For example, if the individual is able to perform eighteen push-ups during the one-minute interval allotted, the individual will input this number of repetitions electronically into the system. The user will then move to another exercise station, such as a piece of equipment or machine in which the user is to curl a given amount of weight for a given number of repetitions. If the user is able to complete those repetitions at that weight within the time period, the user enters in that data. However, if the user is able to only accomplish a portion of the repetitions, that information is entered into the system instead. This information is used to determine if the workout prescription needs to be changed either during the current workout session or more typically in future workout sessions.

The data input provided by the user can be done in any number of different ways, including using at least one electronic device disposed within each booth, such as a data entry screen which is touch activated or has other data input means such as a keyboard disposed adjacent to each workout station or piece of exercise equipment. Centralized or spaced apart kiosks or data entry screens or stations, hand-held or worn electronic devices electronically coupled to the system, etc. could also be used. The computerized system receives this data, in the form of test results and number of repetitions performed which are entered in by the user at each exercise station, and automatically alters the next workout session for that individual. In effect, each workout is building a profile of information to automatically generate the best possible exercise regimen for the next workout session for that particular individual.

Over time, the system will automatically make gradual changes to the number of repetitions or the weight or resistance that is being prescribed for each individual based on the number of repetitions the individual did in a previous workout. Thus, the "stress" or weight resistance and/or repetitions are refined and changed over time in order to be adjusted and meet the needs of the user. Based on the previous repetitions, reaction time, and feedback, the workout program or plan for each individual user will be altered. Thus, as the individual gains strength and/or improves his or her fitness level, the system of the present invention automatically alters and adapts the workout program for that individual so as to continue to challenge the individual and increase his or her strength, fitness level, weight management, etc.

The system of the present invention also incorporates periodization schemes, which alters the stress of training over a period of time. It represents the changes in repetitions and weight or resistance from one workout to the next. Performing the same weight or resistance and repetitions repeatedly over a prolonged period of time provides limited benefits. Periodization provides schemes based upon research that is designed to get the greatest benefits possible for each individual. These periodization schemes can be based upon the individual user's prior feedback and workout plans (general fitness, strength, muscular endurance/toning, weight management, etc.).

Using the information from the assessments (fitness/strength test, prior workout feedback and/or reaction test) enable the creation of the most comprehensive, automated, personalized exercise prescription available to that individual. The system and method of the present invention gives the average person access to an exercise system that is more complex and sophisticated than heretofore known. The system of the present invention takes the exercise science and applies it to each individual to prescribe the best workout program possible for that individual, with the training based on advanced science and collection of specific information, and making adjustments based on that data over time. It is believed that the more advanced the system, the greater the results will be for each individual.

An exemplary exercise regimen that could be incorporated into the invention is illustrated in FIG. 13. Such a regimen could entail the use of up to thirty-five booths, although it will be appreciated that fewer booths could be used, as, for example, the final rest exercise does not need a booth per se and the warmup exercises could be performed in a single booth, and booths are not necessary for rest periods. Approximately thirty seconds to one minute is devoted to each of the exercises listed, so as to provide a workout of between twenty to forty minutes.

It is believed that an exercise regimen having initial stretches and warmup exercises, followed by rest, and then a combination of vibration exercises, in which the user is in contact with a vibrating mechanism, a "push" exercise, a "pull" exercise, a "rotation" exercise, and a "full body" exercise, followed by a rest period and then repeated for the desired length of the workout regimen is very effective. In fact, performing these given exercises in sequence yields greater results than the same exercises performed in a random order. Thus, in one embodiment of the present invention the member performs a vibration-related exercise initially, followed by a "push" exercise, followed by a "pull" exercise, followed by a "rotation" exercise, followed a "full body" exercise before the rest period.

In FIG. 13, the left column represents the actual exercise or stretch performed. The right column represents whether the exercise is a warmup, a rest period, a vibration exercise, a push exercise, a pull exercise, a rotate exercise, or a full body exercise. Preferably, a sequence of exercises is performed in accordance with the sequence provided in the right-hand column. It will be appreciated by those skilled in the art that the exercises in the left column can vary and comprise different vibration, push, pull, rotate, full body, etc. exercises. All or a portion of the exercises may be completed using an exercise device or machine. However, some or all of the exercises may be performed without any exercise device or machine whatsoever.

In accordance with a particularly preferred embodiment of the invention, the sequence of exercises provided in FIG. 13 would be performed in a plurality of booths. The user or gym member would move from booth to booth to perform the different warmup, rest and exercises. The necessary exercise devices and equipment to perform the exercises within the sequence would be provided within the necessary booths. It will be appreciated that the exercises and sequence of exercises provided in FIG. 13 are illustrative only. Different types of exercises or sequences of exercises could also be implemented into the present invention. What is desired is that the user is provided an automatically generated workout regimen by the computerized system and the user performs the workout sequence of exercises within the exercise regimen in order, typically moving from booth to booth to perform the exercises. The workout regimen generated by the computerized system dictates the exercise to be performed, the weight or resistance, and the goal number of repetitions of the exercise within an allotted time period. As such, the user is provided a workout regimen of a sequence of exercises that accomplish the fitness program goal of the user in a very scientific and effective manner with minimal thought and input from the user.

Figure 14:
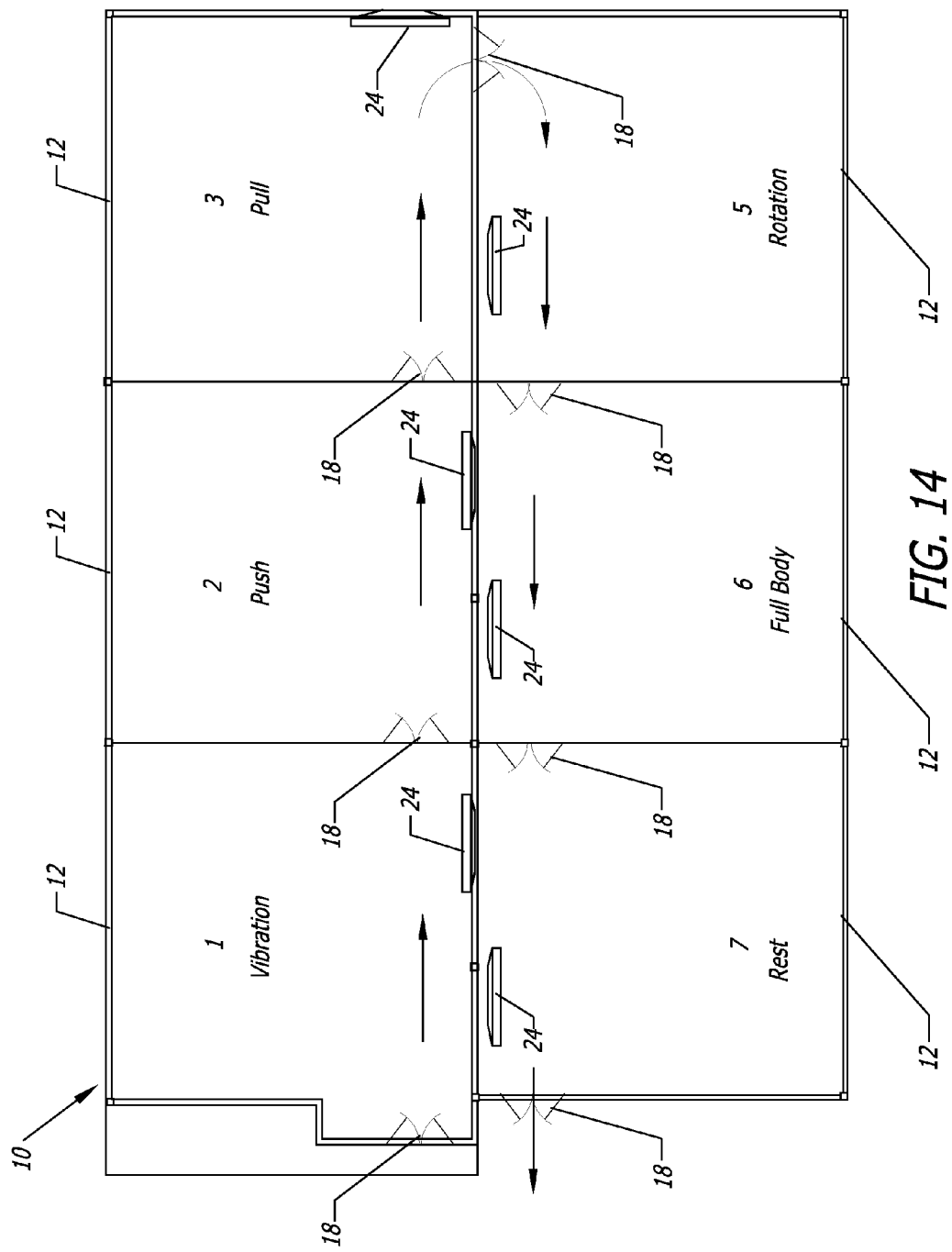
FIG. 14 is a diagrammatic view of a plurality of booths assigned an exercise, in accordance with the present invention.

Although the automatically generated and altered exercise program discussed above could be incorporated into any gym setting, it is particularly suited for the private gym configuration and system having a workout area defined by a plurality of booths, as illustrated and described above with respect to FIGS. 1-12. For example, with reference to FIG. 14, a gym or a section of a gym having only six or seven booths 12 could be used to perform the initial warmup and stretch exercises, and then the vibration, push, pull, rotation, full body exercises, followed by a rest period. The member could perform the sequence of exercises, or any other preset sequence of exercises, and continue to rotate through the booths 12 until the desired number of exercises or total exercise time has been achieved.

With reference again to FIG. 14, it will be seen that a display screen 24 may be positioned within each booth 12. The display screen 24 has input means, such as being an interactive touch screen display. The display 24 will display the workout to be performed by the member, the resistance or weight, and the number of repetitions. Typically, the exercise is timed such that the member will attempt to perform the number of repetitions given by the system within the allotted time. The member will input the actual number of repetitions performed for the given resistance or weight, such that the computerized system can alter future workout regimens based upon the input provided by the member.

Figure 15:
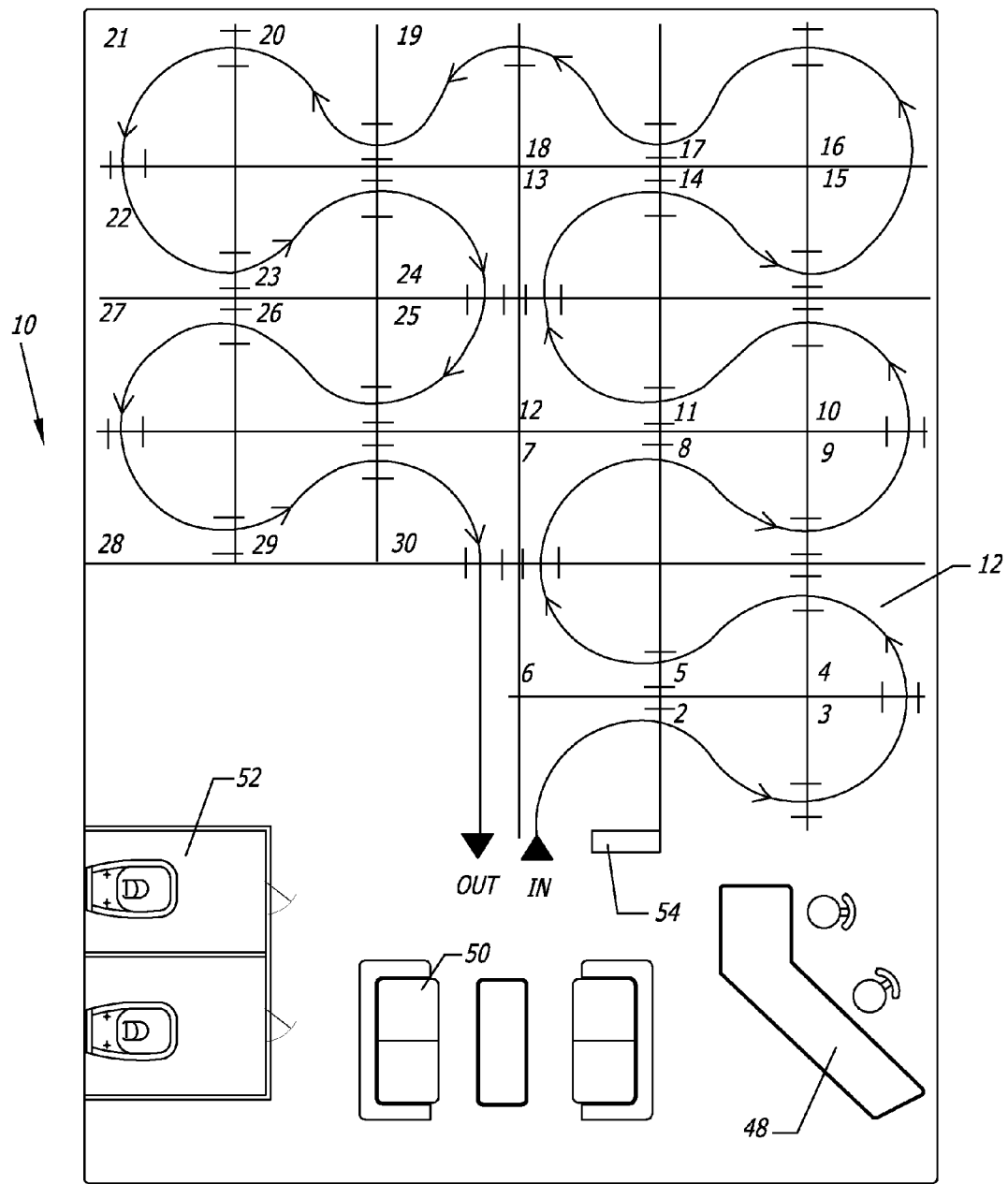
FIG. 15 is a diagrammatic view of an exercise facility embodying the present invention.

With reference now to FIG. 15, although the gym could have as few as six booths to accomplish the present invention, in a more particularly preferred embodiment of the present invention, the gym 10 has a sufficient number of booths that an entire workout regimen can be performed by moving from one booth to another until the entire workout sequence is achieved.

The gym 10 will typically have a reception desk 48 with employees available to register the member, assist the member in beginning the workout, etc. A waiting room 50 and restrooms 52 will typically be provided. A kiosk or display monitor or the like 54 may be provided, such as outside the initial booth, for the member to log in and perform a reaction test. The member then proceeds through the various booths 12 (numbered 1-30 in FIG. 15), performing a different exercise or a rest period. In the case of providing one minute of time to perform the exercises or rest within each booth 12, in the arrangement illustrated in FIG. 15, the member's workout would last thirty minutes.

Although only one member would be in a given booth 12 at any given time, it will be appreciated that multiple members could be exercising within the booths and the gym at the same time, but be present in different booths so as to follow the sequence of other members. In the arrangement illustrated in FIG. 15, with a total of thirty booths, up to thirty gym members could be present and performing their exercises according to their individualized workout regimens at any given time. Of course, when the first member left the last booth, another member could enter into the first booth to begin his or her workout regimen. The computerized system of the present invention allows members to schedule a specific time to begin their workout, and then moves that member from the first booth through each of the series of booths until the workout session is completed. It will be appreciated that each booth at any given moment may have a different member of the gym therein performing an exercise. All of the exercises are specifically timed, such that each gym member in a given sequence or series of booths finishes his or her exercise for that specific booth at the same time, and is provided an allotted amount of time to enter in the results of their exercise, typically in the form of the number of repetitions performed. All of the gym members are then given an allotted time to move to the next booth, such that gym members are moving from one booth to another at approximately the same time, such that there is only a single member within a booth at a given time.

It will be appreciated that each booth 12 includes a workout station, which can comprise a mat for performing stretches or manual exercises, such as sit-ups, push-ups, etc. Alternatively, an exercise device or piece of machinery is disposed within each booth for performing a particular exercise. Typically, only a single piece of exercise equipment or machine is in each booth, such that the user performs only a single exercise, according to the repetition and resistance/weight provided by the personalized exercise regimen. In a particularly preferred embodiment, each member would go through a series of warmup exercises or stretches, and then vibration, push, pull, rotate and full body exercises, resting between each set of sequences, in order to achieve a maximum benefit workout in the allotted time, although other exercise sequences and regimens are contemplated by the invention.

Figure 16:
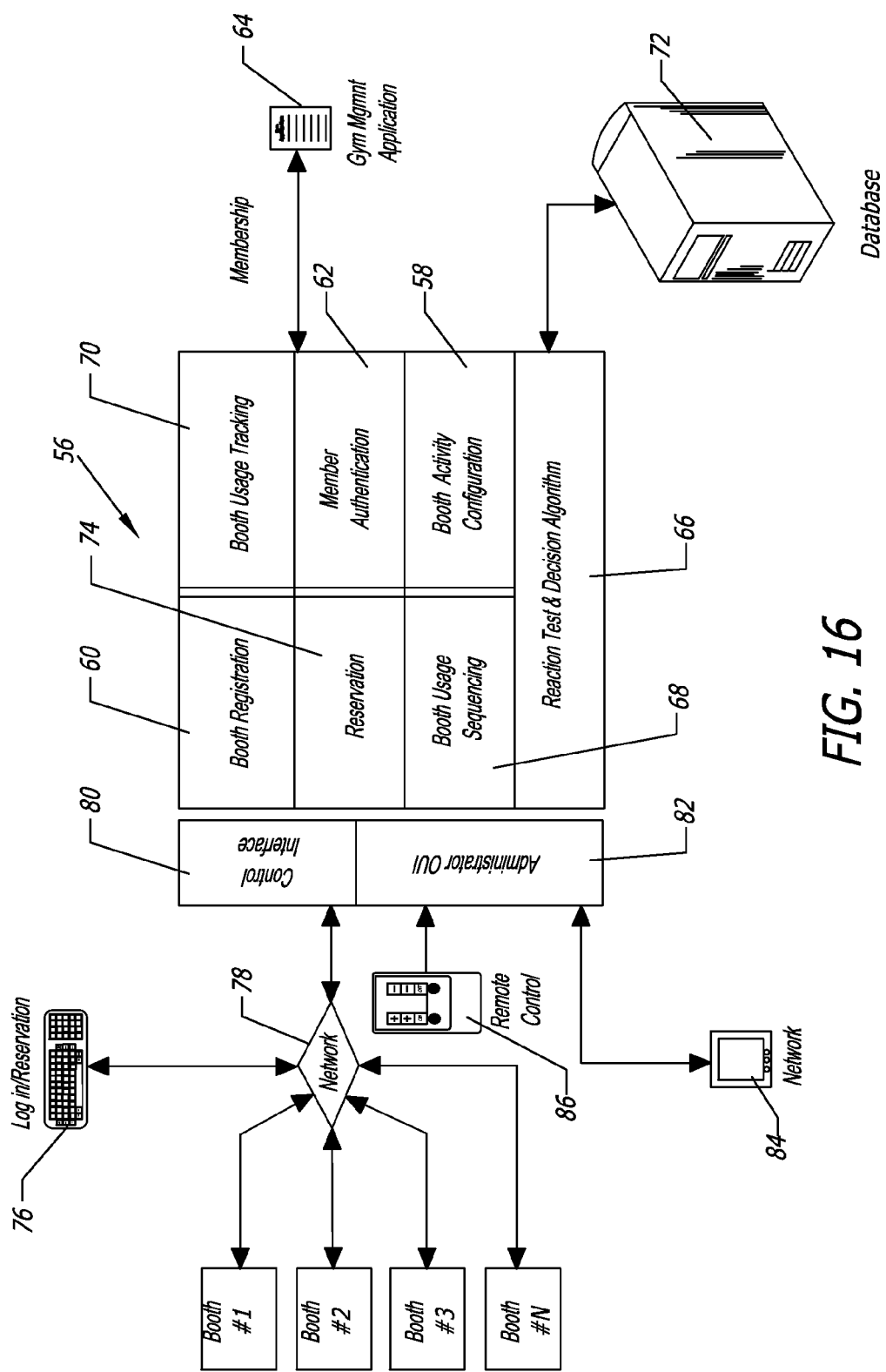
FIG. 16 is a diagrammatic view illustrating a computerized system used in accordance with the present invention.

With reference now to FIG. 16, an electronic framework of the computerized system utilized in accordance with the present invention is illustrated. This includes the booth application server 56, which may represent a central computer for each gym or location. It is also to be understood that the server 56 could represent additional servers or computers which are connected to the computers, or otherwise receive the information, from the individual gym locations. Clients or users access the server or computers from access channels such as the interactive kiosks or screens within the booths or placed in common areas, via the user's computer and an Internet network connection, or via mobile application or the like.

The server 56 includes a booth activity configuration module or algorithm 58, which allows the administrator to define the activity for each of the booths and also have relevant information like video or audio tagged to such activities which will be rendered to the user while he is performing the workout. Booth registration module 60 enables the client to invoke the server and have the activity-related information like the video/audio or other relevant content downloaded locally to the respective booth CPU 34 associated with each display 24. Authentication module 62 performs member identification, number, card swipe, electronic chip reading, etc. by interfacing with a third-party gym management software 64. The reaction test module 66 of the server and system provides the capability to prompt the user to go through a reaction test, which shall in turn determine the quantity of reps and resistance/weight he or she needs to do for each of the exercises of the user's personalized workout regimen. A decision algorithm stored on the server or other computer shall have the capability to take the inputs from the reaction test and the historical data of the user from his or her previous workouts and generate and define the quantity of reps and resistance for each of the exercises.

The system shall have the ability to take the user's exercise performance results for each of the booths' exercises attempted and track the usage and build the capability of sequencing 68 from one booth to the next. The booth, display, mobile applications, etc. shall provide easy interactive and ubiquitous ways to drive the user's experience while managing various aspects like authenticate, validate through reaction tests and guide the user by suggesting appropriate workout regimes.

The server 56 has a variety of configurations and purposes. These include a booth registration 60, wherein the capability is provided to have the exercise and respective information like video data localized and stored in the local database which will avoid the overhead of streaming the video from the server in real time which could hamper the user's experience. Once a particular booth is registered and mapped to a certain exercise activity, the application server pushes the data related to the exercise activity onto the local database and computer associated with the booth and touch screen/kiosk, and the user will render it from the local system.

Thus, the system, in order to achieve this, has the ability to define the booth setup procedure followed by initialization process where the booth number shall be entered and submitted by the administrator. The server shall validate the request and push the respective data related to the activity that is mapped onto the client's local database. For example, if the administrator inputs the booth number 6, then the relevant exercise activity is mapped to booth 6 on the booth application server and pushed to the client database along with the video and audio and other information related to that booth.

The server also verifies and authenticates the user 62 by validating the entered member identification and/or password prior to the start of the booth usage. This may be done with a third-party gym management application software, as illustrated in FIG. 16.

The server tracks the booth activity configuration 58. Each activity or exercise that is offered at the facility such as bench press, push-ups, curls, etc. needs to be defined in the system and should be mapped to the respective booth. The server can accommodate any number of booths, such as booths 1-90, and map each one to an activity where the activity need not be a unique entity. For example, the activity called "bench press" may be mapped to both booth number 1 as well as booth number 18, or later changed from booth number 1 to booth number 7. The booth activity configuration tracks the booth number, the activity type, the benefits of the activity, and the video and/or audio feeds that are tagged to this workout or booth.

The system shall provide the capability to configure a reaction test 66 which shall be prompted to the user and capture the inputs to evaluate the responsiveness to define the quantity of reps or sets or weight or resistance that he or she will need to do for each of the activities in the exercise program generated by the system. A decision-based algorithm is constructed based on the physiological sequence scheme mapping based on the reaction test and historical data of the consumer's earlier workout capability to arrive at the quantity of the reps and sets and/or resistance/weights for each of the activities.

The server also tracks booth usage 70. An individual should be authenticated at the kiosk or booth for member identification and only after successful identification will he or she be able to proceed further. A typical process flow to the booth usage tracking is that the member arrives at the facility for his or her regular workout regime. The member arrives at the kiosk or booth where he or she will be prompted to validate his or her identity by entering the member identification. The system proceeds to prompt the user to go through the reaction test. Based on the inputs provided by the user on the reaction test, the system arrives at the quantity of the reps or sets that the user needs to do for each of the activities at each booth. The booth will then prompt the user to start the activity defined as part of booth number 1 and also display the time in which he will need to complete the activity. On completion of the defined time for the booth number 1 activity, the system shall prompt the user to enter the details of the workout that was achieved within the allotted time. The member user shall enter the details of the workout achieved, typically only the number of repetitions performed, and submit the request. The system will then instruct the user to move to the next booth, i.e., booth number 2, where the user will have a defined time gap to move from one booth to the next, which time is typically displayed on the countdown timer of the screen. The user shall then move to the next booth and continue the defined activity and continue this process until the user completes all of the booths for that particular day. It will be appreciated that all members of the gym within the booths are working out in a similar fashion and are timed in sequence through the booths in a coordinated manner.

The system may provide rest or gaps for every booth, as described above, and the user shall be displayed sequence scorecards where he or she will have the ability to review any of the booth scores and update the data as necessary, as described above. The system also provides the capability of the users to view previous history of the workouts done, either at the gym facility or via the user's computer or hand-held device via a mobile application.

The booth server shall have the capability to manage the sequence and timing of the booths across multiple users who are using the booths and queue them accordingly. If there are 30 booths and 30 members that are currently accessing them, then the system shall appropriately time the queue to ensure there will be no overlapping of the booth sequence across multiple users.

Figure 32:
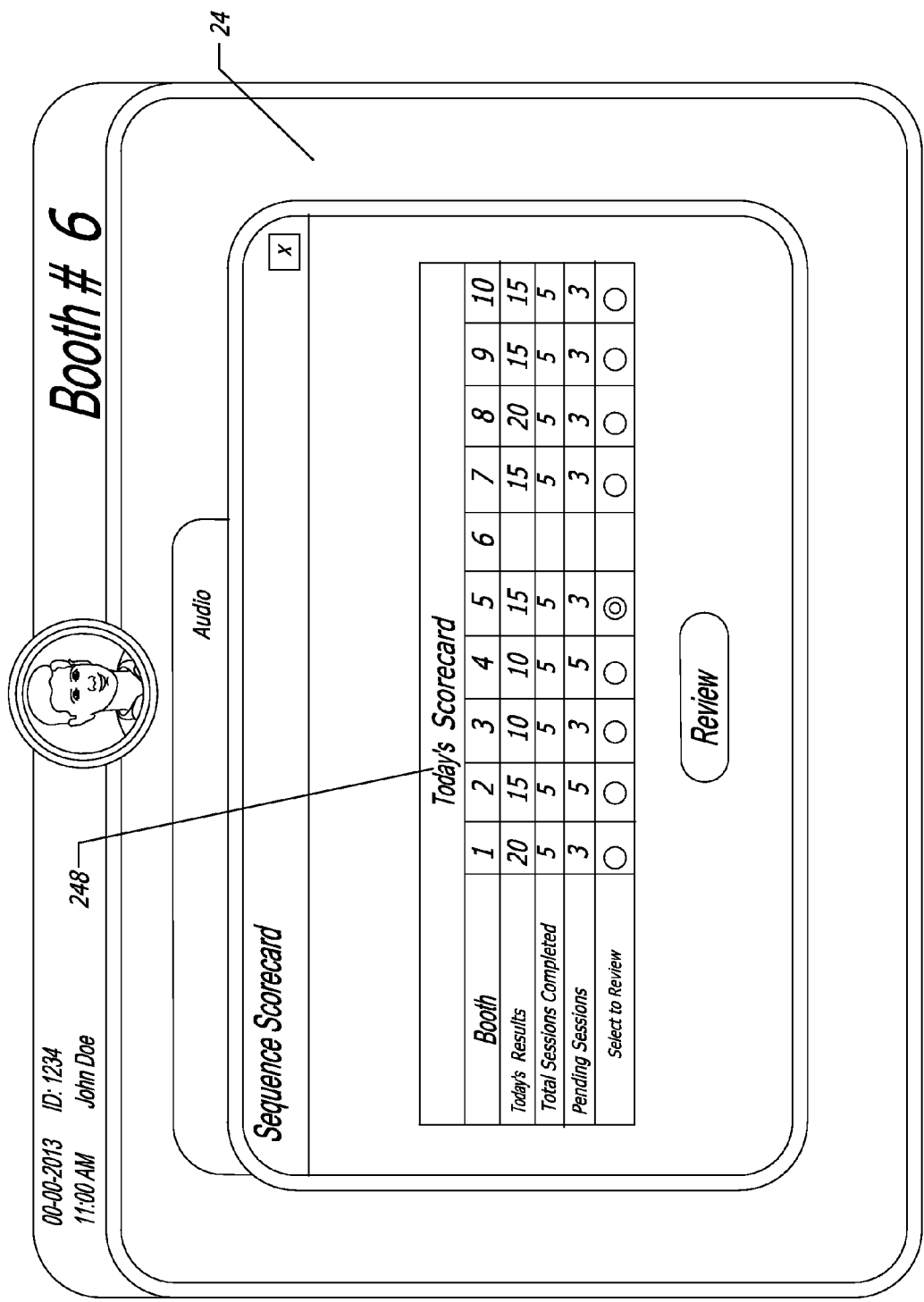
FIG. 32 is a diagrammatic view of a display of an electronic screen providing a sequence scorecard or summary of the user's exercise regimen for a particular day.
Figure 33:
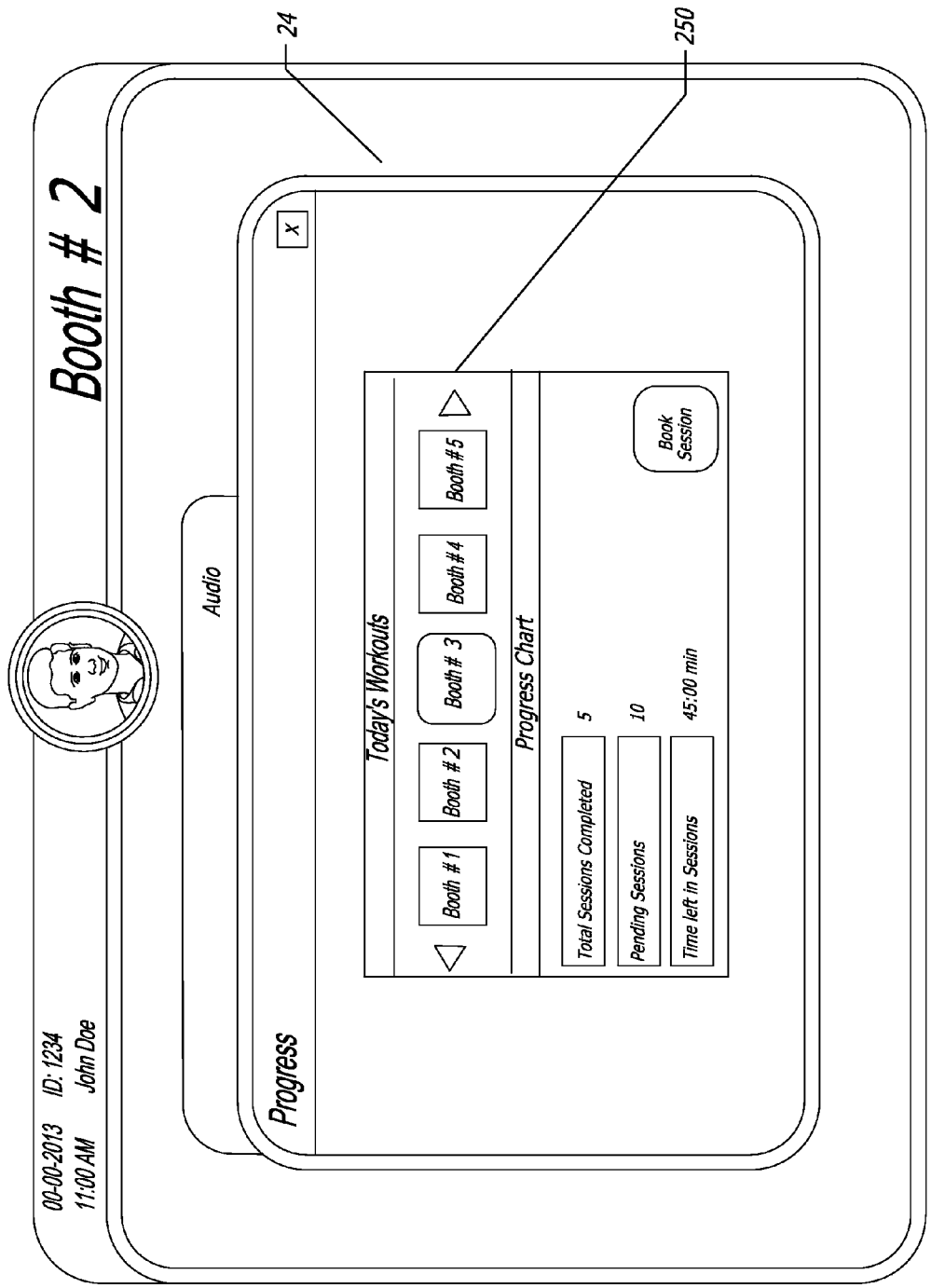
FIG. 33 is a diagrammatic view of a display of an electronic screen providing user exercise performance results feedback, in accordance with the present invention.

Typically, after user authentication, the system has a defined time for the start of the first booth. The system then has a defined time for the member to move from one booth to the next. After every five booths, the sixth booth may be a rest period for the member. This time period can be used by the user to review his achievement, as illustrated in FIGS. 32 and 33, before moving on to the next booth. To ensure the sequencing and timing is managed, the system tracks the start of the event for every booth at the start of the countdown timer and end of the event at the end of countdown timer for every booth.

Although rest periods may be built into the exercise regimen, a rest period is not necessarily essential. The computer algorithms of the system can be changed periodically as new data and information on exercise science is advanced. Each gym's computerized system may be in communication with a central server or a server based in the cloud which can dictate the changes to the workout regimens, exercises to be performed throughout the sequence of booths, etc. Preferably, a member's data and exercise regimens are also stored on a cloud-based or central server, such that the member could visit other gym locations and obtain their exact data and up-to-date workout regimen at any of the gym facilities incorporating the present invention.

As will be described herein, the server includes or is coupled to a database 72 which contains the member's registration information and periodically updated workout regimens. A reservation module 74 allows the members to reserve a time to begin exercising at the gym. The log in reservation 76 may be done at the gym, or away from the gym, such as at home using the member's computer, or even by means of a smart phone or hand-held electronic device. The user logs in to a network 78 which interfaces with the server 56 and the various booths (labeled 1-N). An interface 80 is provided between the networks 78, the log in/reservation means 76 and the booths, etc. An administrator may be provided an interface 82 as well, such as via network 84. This may be done by remote control 86 or at the gym.

Figure 17:
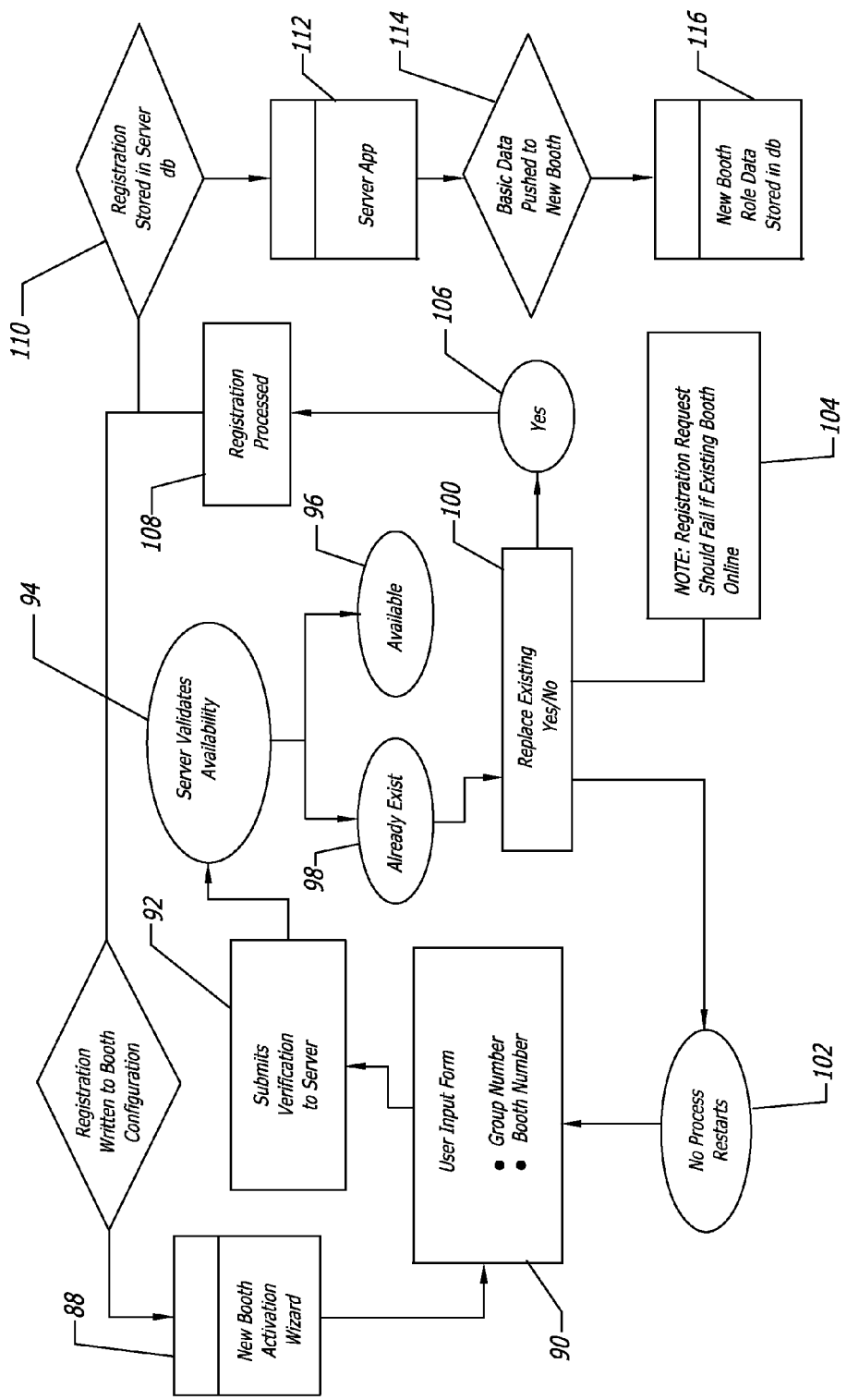
FIG. 17 is a flowchart depicting the steps taken in assigning exercises to a plurality of booths used in accordance with the present invention.

With reference to FIG. 17, software is used in accordance with the present invention to initialize new booths and the booth configuration. The new booth activation wizard 88 receives a user input form providing the group number and the booth number 90. Verification is sent to the server 92. The server validates the availability of the booth 94, and indicates if the new booth is available 96, or is already in existence 98. If it is already in existence, an inquiry is provided asking whether to replace the existing booth 100. If no, the process restarts 102. If the new booth registration request is being conducted while the booth is online and being used (104), registration cannot be completed. However, if this is not the case, and if the administrator desires to replace the existing booth 106, the registration process is started 108, and the registration is stored in the server database 110. The relevant server application software 112 then pushes the basic data to the new booth 114, after which the new booth roll data is stored in the database 116.

Thus, in accordance with the method shown in FIG. 17, a new booth can be added to an existing series of booths, or a booth can be reassigned a piece of exercise equipment or an exercise, and tracked within the server and system in accordance with the method of FIG. 17, such that the computerized system can coordinate the sequence of the user's personalized exercise regimens with the exercises and exercise devices assigned to the booths.

Figure 18:
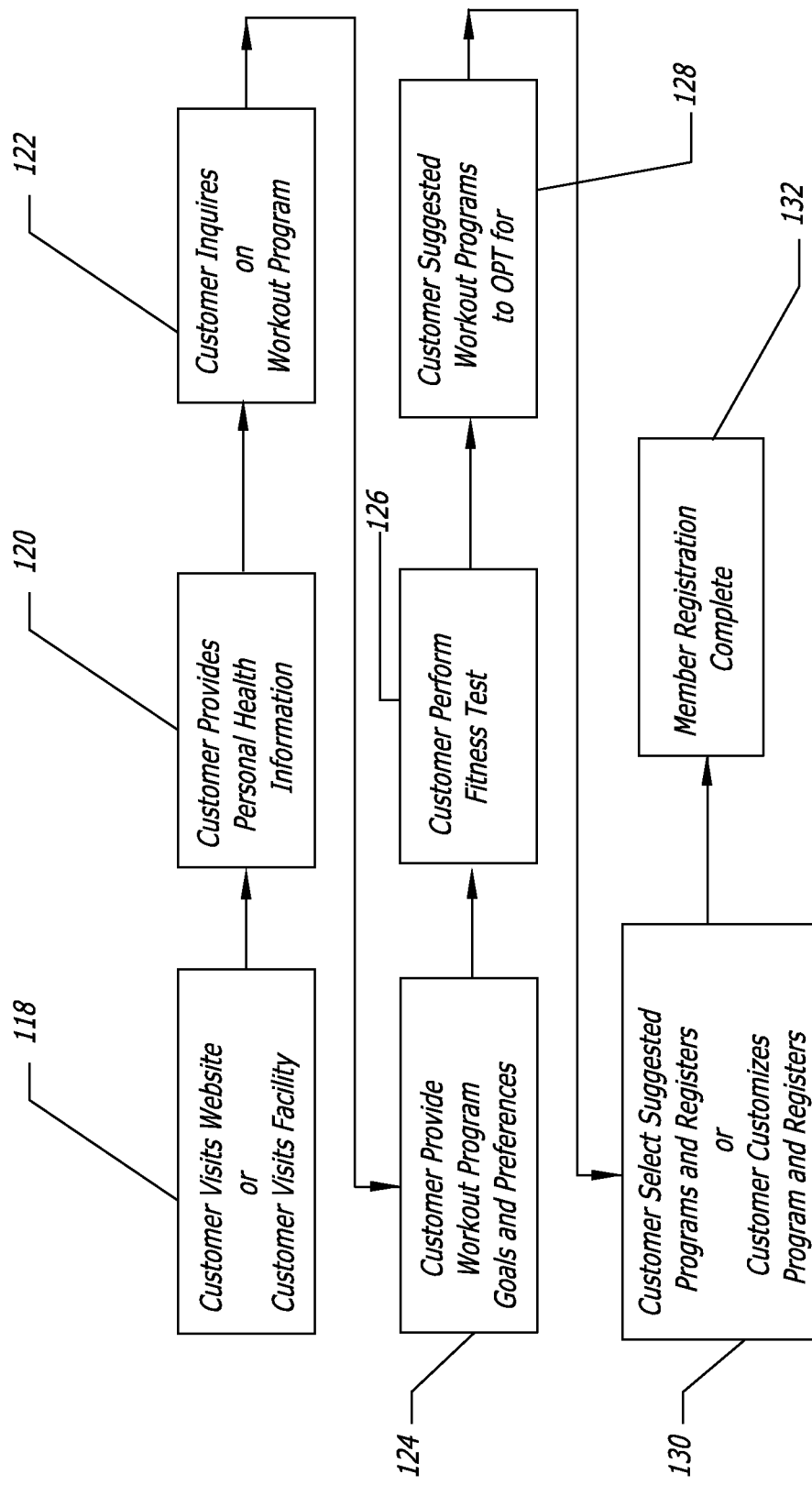
FIG. 18 is a flowchart depicting the steps of a member or user registration, in accordance with the present invention.

With reference now to FIG. 18, the steps undertaken in registering a member are shown. The customer visits the website or visits the gym facility 118. The customer provides personal health information 120. The customer inquires regarding the workout program 122. The customer provides workout program goals and preferences 124. The customer then performs the fitness test 126, such as the grip test, which is performed at the gym facility. A suggested workout program is provided to the customer to opt into 128. The customer selects one of the suggested programs and registers, or customizes a program and registers 130, which completes member registration 132.

Figure 19:
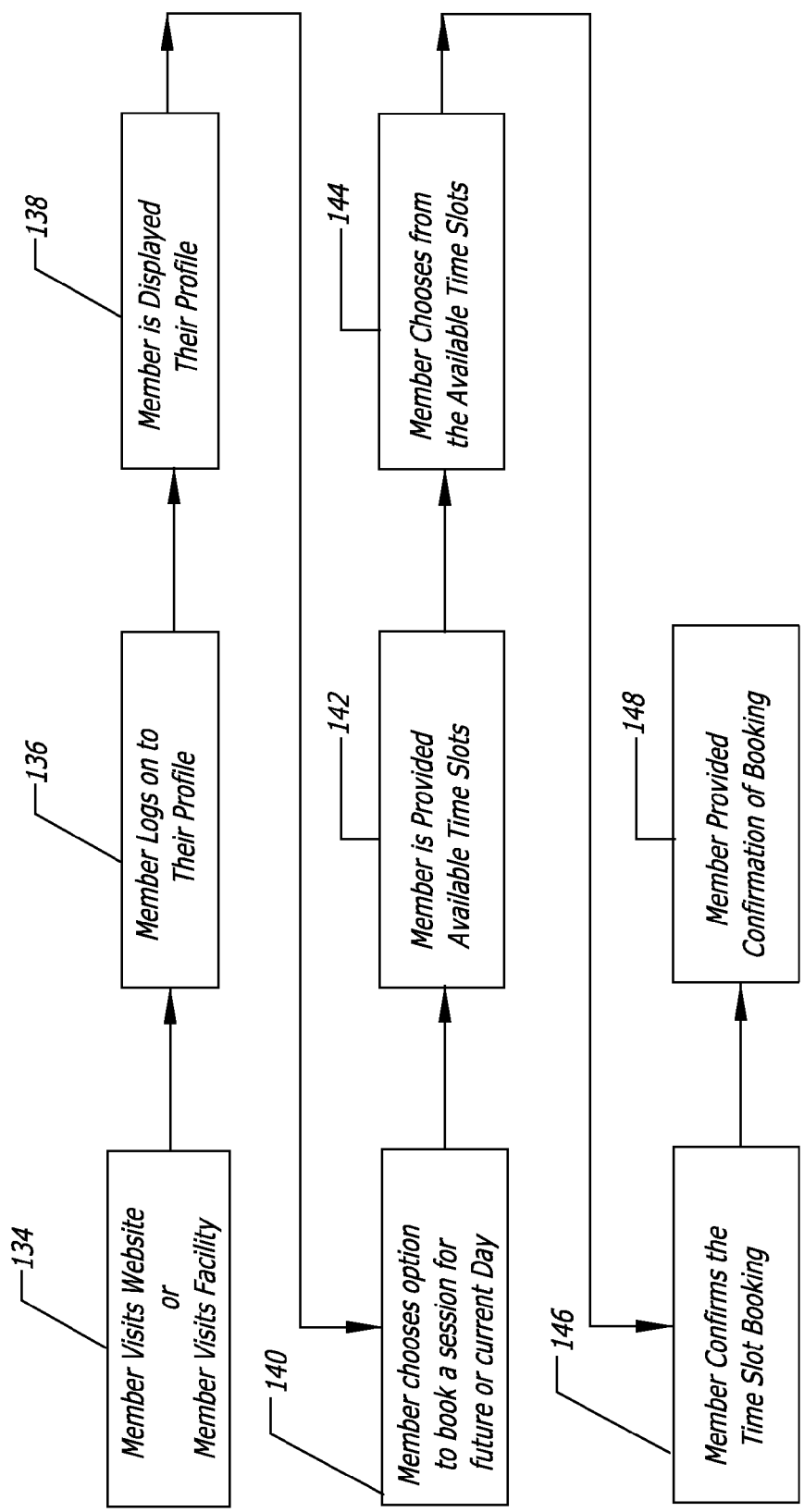
FIG. 19 is a flowchart depicting making reservations for the exercise facility of the present invention.

With reference now to FIG. 19, the steps undertaken to reserve gym time is shown. The member visits the website or gym facility 134. The member logs onto their profile which was provided during the registration process 136. The member is displayed their profile 138, and chooses an option to book a session for a future or current day 140. The member is provided available time slots 142 to begin his or her workout. The member chooses from the available time slots 144. The member then confirms the time slot for booking 146, and the member is provided confirmation of the booking 148.

FIG. 20 illustrates exemplary members which have reserved and booked time slots. In the example provided in FIG. 20, members John, Tom and Jane start at booth 1 at 9:00 am, 9:01:20, and 9:02:40, respectively, thus being spaced from one another by one minute and twenty seconds. Assuming that the member is in each booth for a total time of one minute, this would provide twenty seconds for each member to input their results and move to the next booth after their exercise is completed in that booth.

Figure 21:
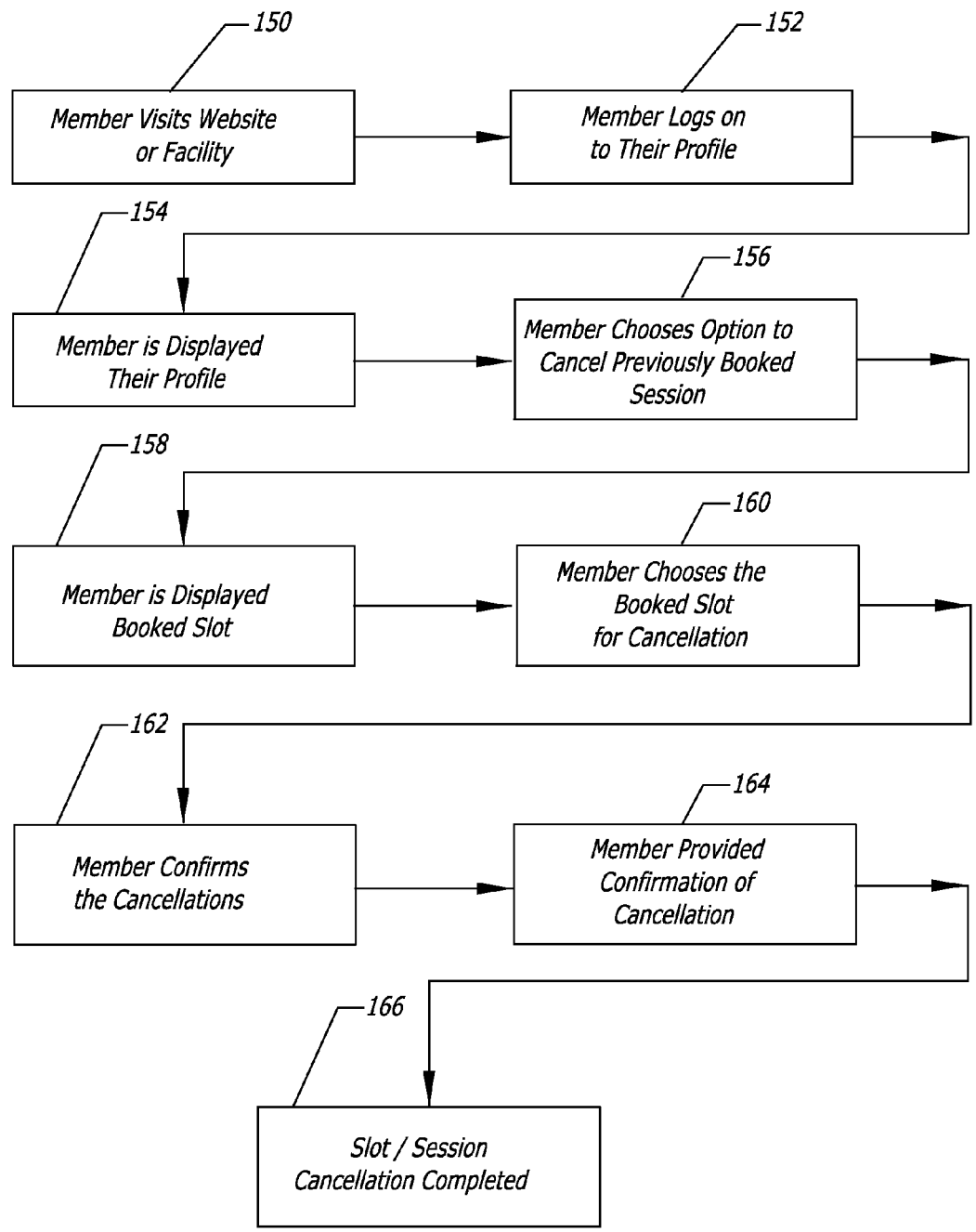
FIG. 21 is a flowchart depicting the steps taken in cancelling an exercise session using the present invention.

With reference now to FIG. 21, in order to cancel a previously-booked time slot, the member visits the website or gym facility 150. The member logs on to their profile 152 and after being displayed their profile 154, chooses the option to cancel a previously-booked session 156. The member is displayed the booked slot 158, and chooses the booked slot for cancellation 160. The member confirms the cancellation 162, and is provided a confirmation of the cancellation 164. The slot or session cancellation is then completed, and the slot or session is made available by the system to other gym members.

Figure 22:
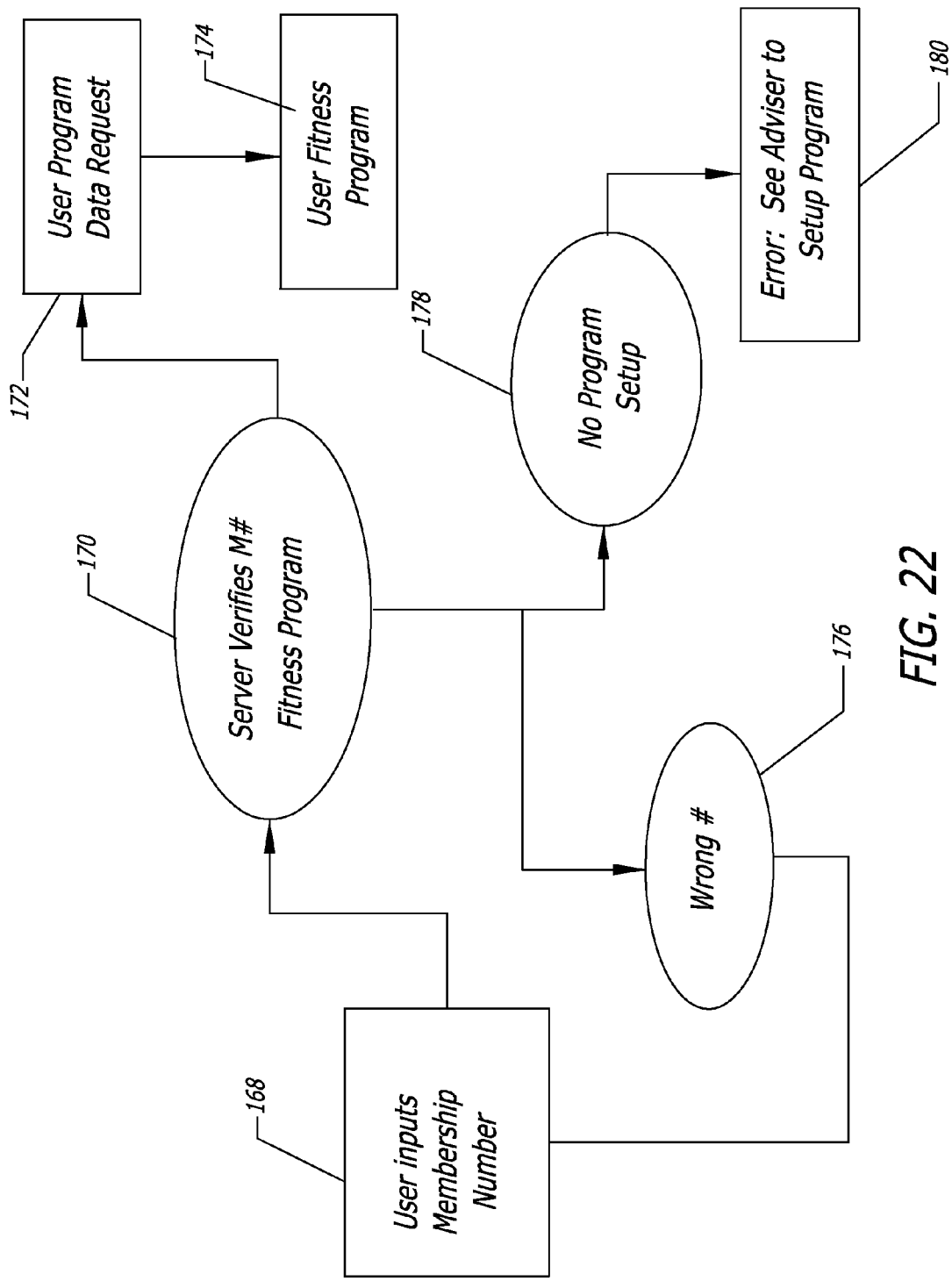
FIG. 22 is a flowchart depicting selection and assignment of a fitness program, in accordance with the present invention.

With reference to FIG. 22, whenever a user inputs their membership number 168, the system or server verifies the membership number and fitness program 170. Information is provided as part of the profile, including the user or member's program data request 172, which includes the user's fitness program 174. If the member enters the wrong membership number 176, the user is prompted to input the membership number again 168. If a user profile is not retrieved, and a program is not set up 178, the member is prompted to see an advisor to set up the program and possibly provide missing information during another registration process 180.

Figure 23:
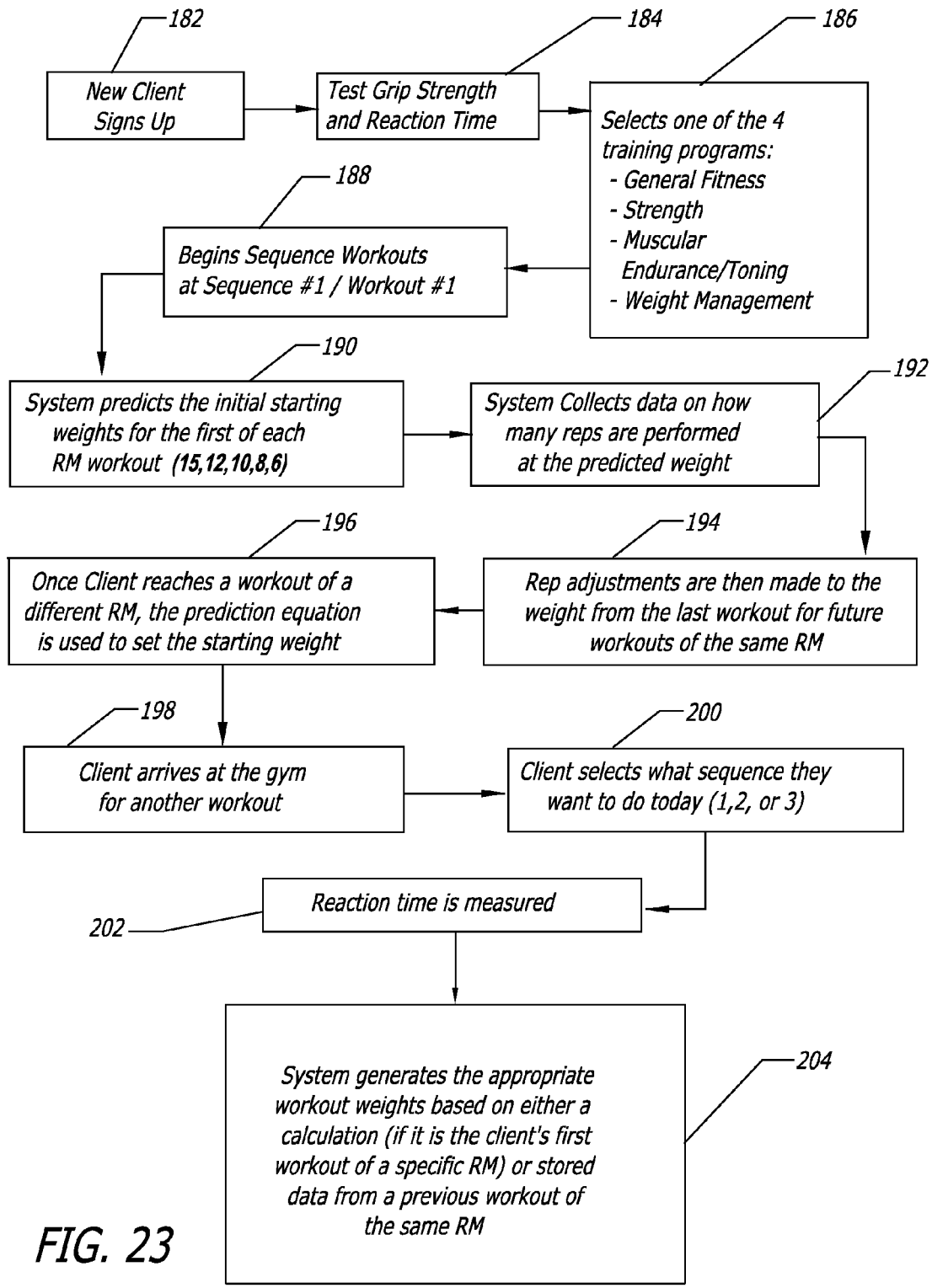
FIG. 23 is a flowchart depicting the steps taken in connection with automatically generating or modifying an exercise regimen for a user of the invention.

With reference now to FIG. 23, when a new member signs up 182, as part of the registration process, as indicated above, the member performs a grip strength test and reaction time 184. The member may then be provided a selection of training programs, such as general fitness, strength, muscular endurance/toning, and weight management. The algorithms of the system will determine the amount of weight or resistance and the number of repetitions for each exercise depending upon the training or fitness program selected, user fitness test results, and user-related information provided during the registration process. For example, if the potential member is looking to add strength, the weight or resistance may be increased. However, if the potential member is looking for weight management or endurance, the weight or resistance may be lessened and the number of repetitions increased.

With continuing reference to FIG. 23, if the newly-registered member desires to work out that very moment, the system creates a sequence of workouts beginning with sequence number one, workout number one 188. The system predicts the initial starting weights for the first of each repetition maximum workout 190. These may be, for example, reps of six, eight, ten, twelve or fifteen depending upon the member's results of the grip strength test and reaction time, as well as the training program selected. The system then collects data on how many reps are performed at the predicted weight 192 as the member completes a given workout and provides the input into the system. Repetition adjustments are then made to the weight from the last workout for future workouts of the same repetition maximum 194. Once the member reaches a workout of a different repetition maximum, the prediction equation is used to set the starting weight 196.

When the member arrives at the gym on another day for another workout 198, the member may select which sequence they want to do that day 200. In a particularly preferred embodiment, the gym will be set up such that several sequences of booths are presented. For example, each sequence may include up to thirty booths, or will have a lower number of booths that may be repeated. Each sequence may be directed to and include different exercises or machines which can be used to exercise an individual in a distinct way as compared to the other sequences. For example, in sequence number one the exercises might be more tailored to emphasize a chest and back workout, whereas the exercises performed in sequence number two are biceps and triceps or leg intensive. Alternatively, each set of booths is directed to a different training or fitness program. A reaction test is given 202, and the system generates the appropriate workout weights based on either a calculation (if it is the member's first workout of a specific repetition maximum) or stored data from a previous workout of the same repetition maximum 204.

Figure 24:
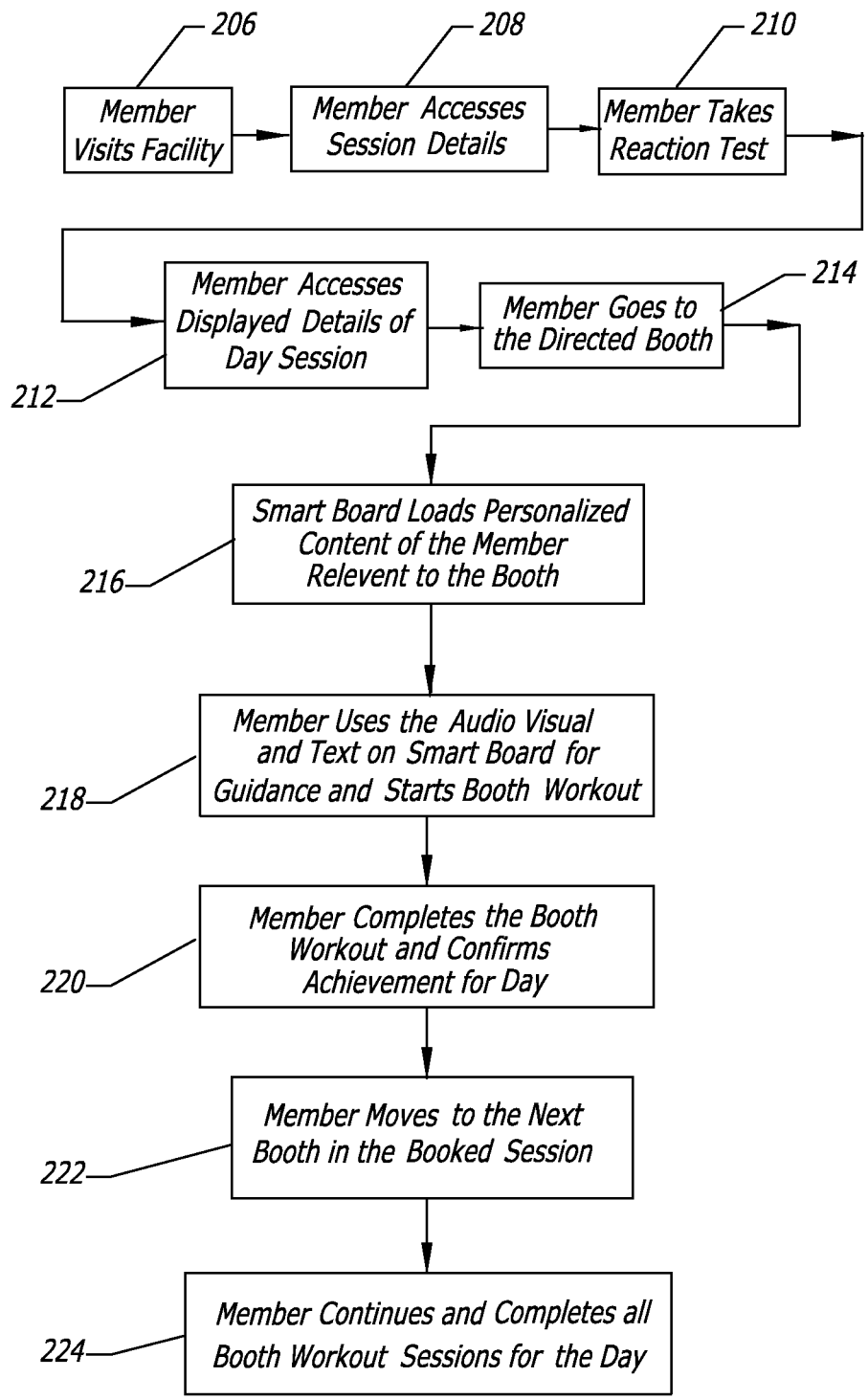
FIG. 24 is a flowchart depicting the steps taken in connection with a user or member being advanced through the booths of the present invention.

With reference now to FIG. 24, when a member visits the gym facility 206 to begin a workout, which has typically been booked in advance, the member accesses the session details 208. The member takes the reaction test 210, either outside of the first booth or within the first booth. The system will automatically generate the appropriate workout regimen based upon the selected sequence, reaction time, and data stored from previous workouts by that user. The member may access and be displayed the details of the day's workout session 212.

The member goes to the directed booth 214. A smart board associated with that booth loads the personalized content of the member relevant to that booth 216 from the server or other computerized network system. The member uses the audio visual and text on the smart board or electronic display screen for guidance as a tutorial and starts the booth workout 218. The member then completes the booth workout and confirms the achievement in the form of exercise performance results for the day. This is typically done by entering the number of repetitions for the given weight or resistance for the exercise assigned to that booth. This is entered into the computerized system using an electronic device, such as the electronic touch screen. The member moves to the next booth in the booked session 222, and continues and completes all booth workout session for the day 224. It is possible, and in fact preferable, that as a member leaves a given booth, a member who was just performing exercises in the immediately preceding booth will enter into that booth. Thus, it is quite possible that each gym member continues and completes all of the booth workout sessions for the day without any interaction with any other gym member, and possibly not even see any other gym member.

Figure 25:
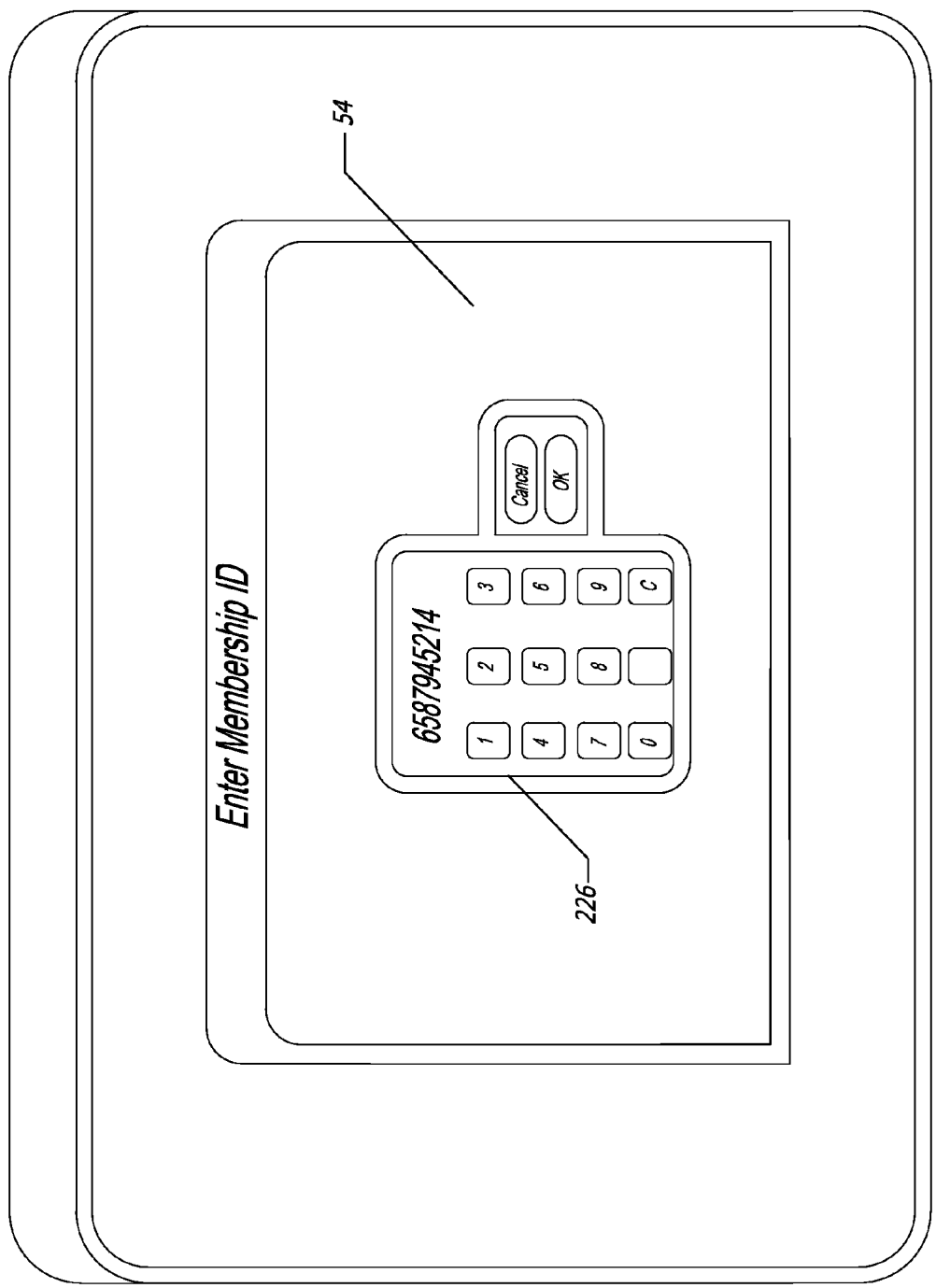
FIG. 25 is a diagrammatic illustration depicting an electronic display screen for entering a user's membership identification.
Figure 26:
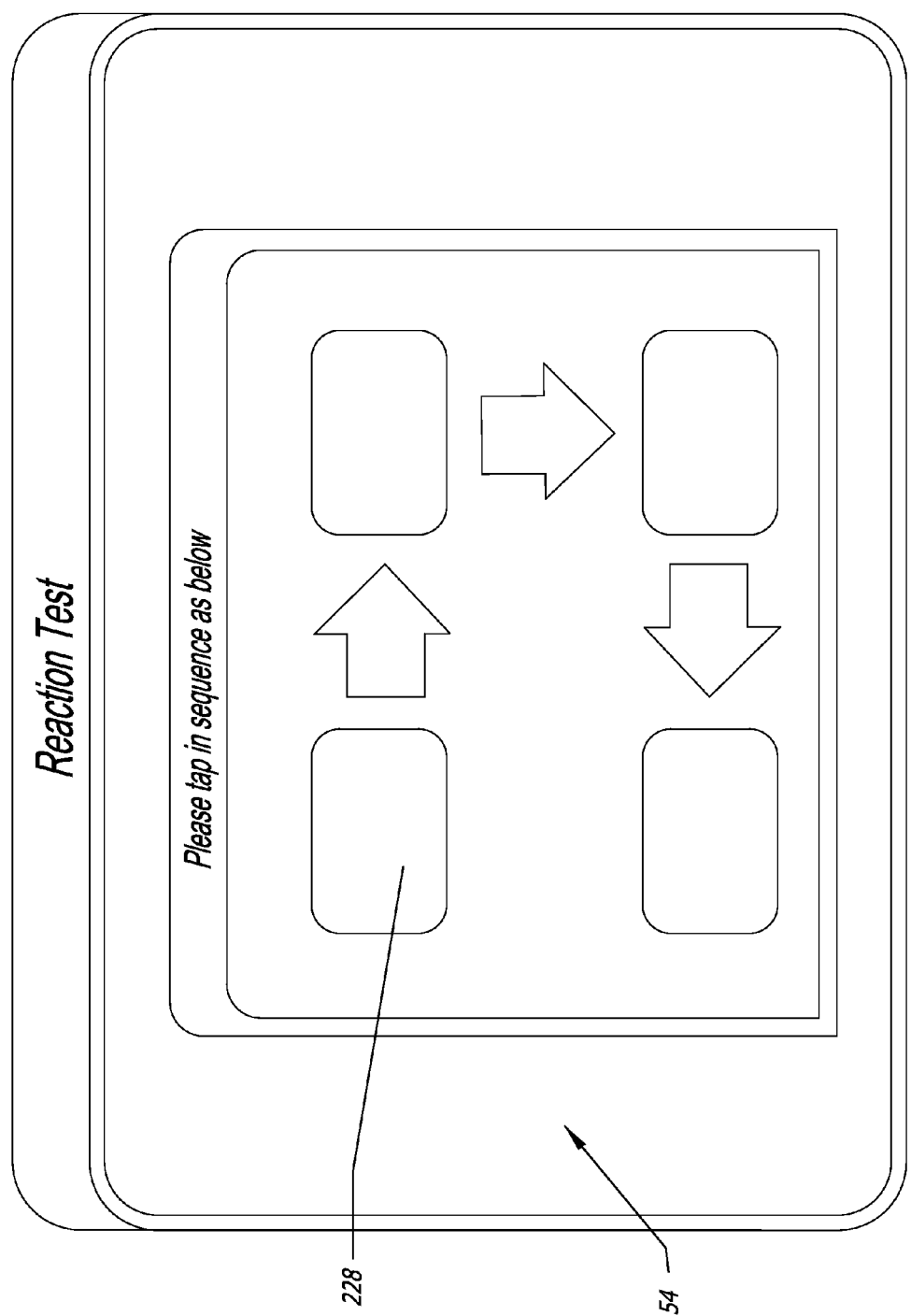
FIG. 26 is diagrammatic view of an electronic screen displaying a reaction test to be taken by the user prior to exercising.
Figure 27:
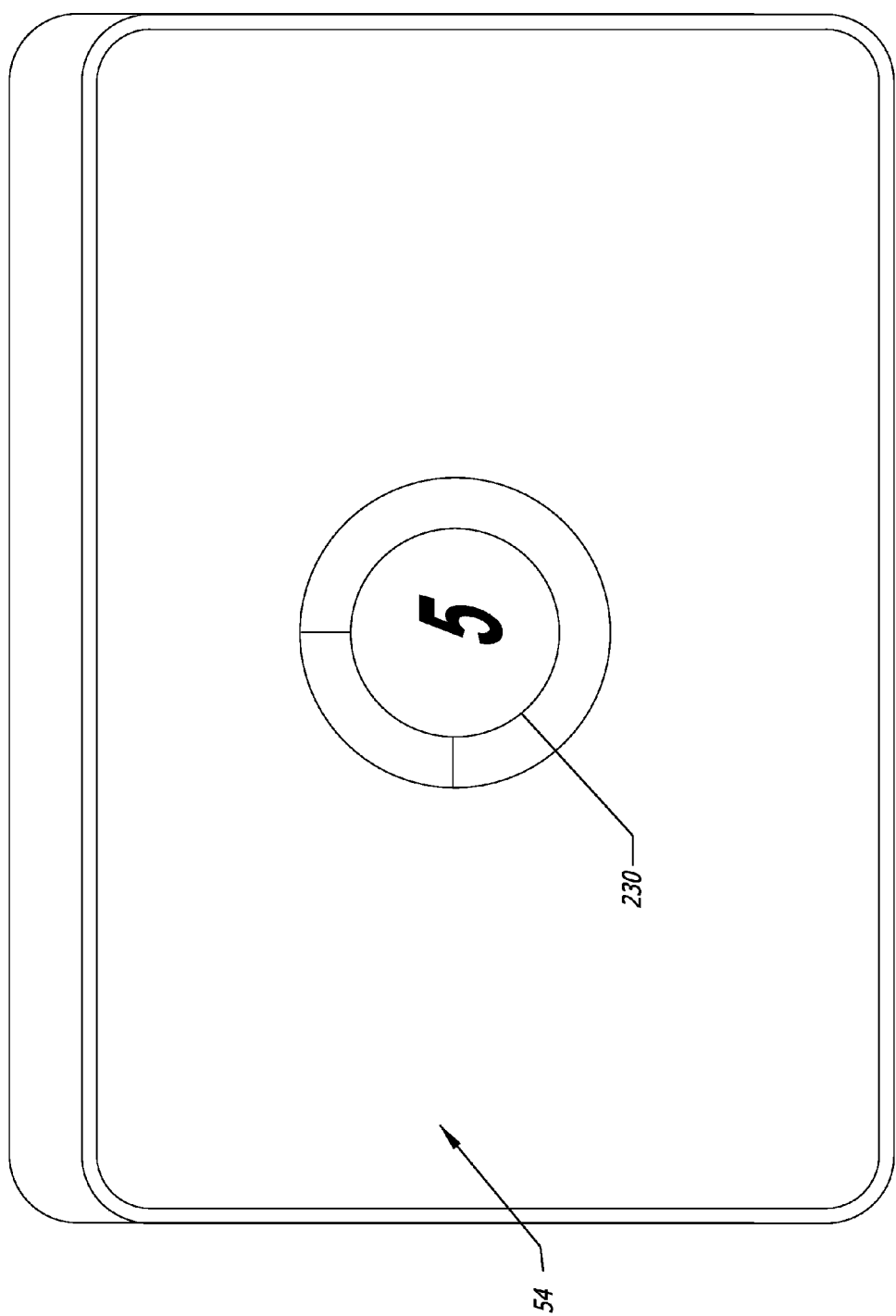
FIG. 27 is a depiction of an electronic screen providing a timer prior to entering a booth of the exercise facility.

The steps illustrated and described in FIGS. 23 and 24 are graphically shown in FIGS. 25-33. With reference to FIG. 25, the user is prompted to enter his or her membership identification in a kiosk or touch screen display 54, such as a touch keypad or data entry box 226. As illustrated in FIG. 26, a reaction test is performed. This may be, as illustrated, tapping the sequence of the lighted icons 228 in a given order. As illustrated in FIG. 27, a timer 230 may be used to indicate how many seconds or minutes the member has until entering the first booth.

Figure 28:
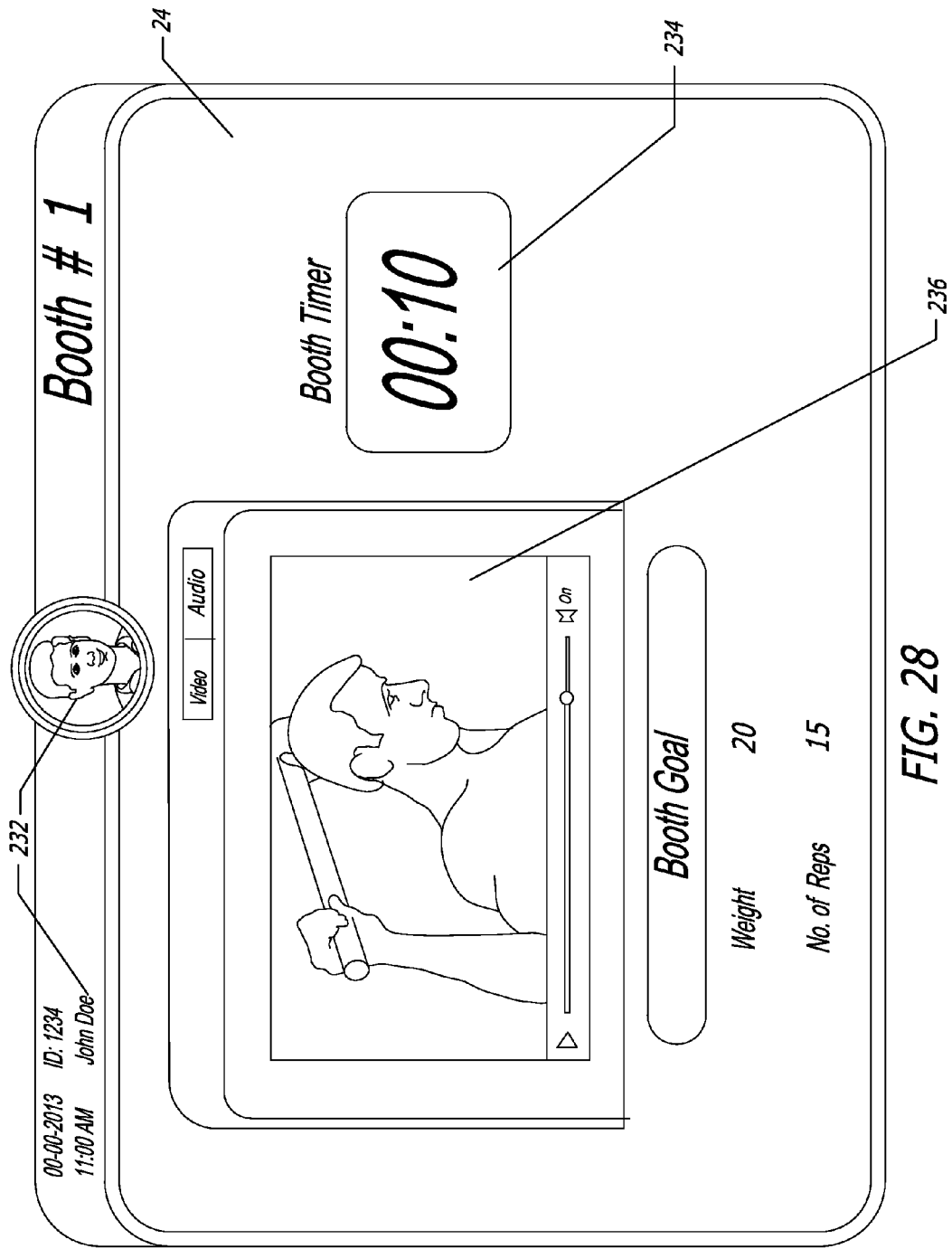
FIG. 28 is a diagram illustrating the display of an electronic screen within the booth and used in accordance with the present invention.

With reference to FIG. 28, upon entering the first booth, the display screen 24 identifies the member, such as by ID number, name, or even by a photo 232 which has been previously taken of the member. In this manner, the member knows that the system is synched to the member and the first booth. The display screen 24 displays a timer 234 and the individual's previously-calculated goals as far as number of repetitions and the given weight or resistance. A tutorial video 236 is provided to show the member how to perform the exercises, and if necessary how to operate the exercise device or machine to perform the exercises.

Figure 29:
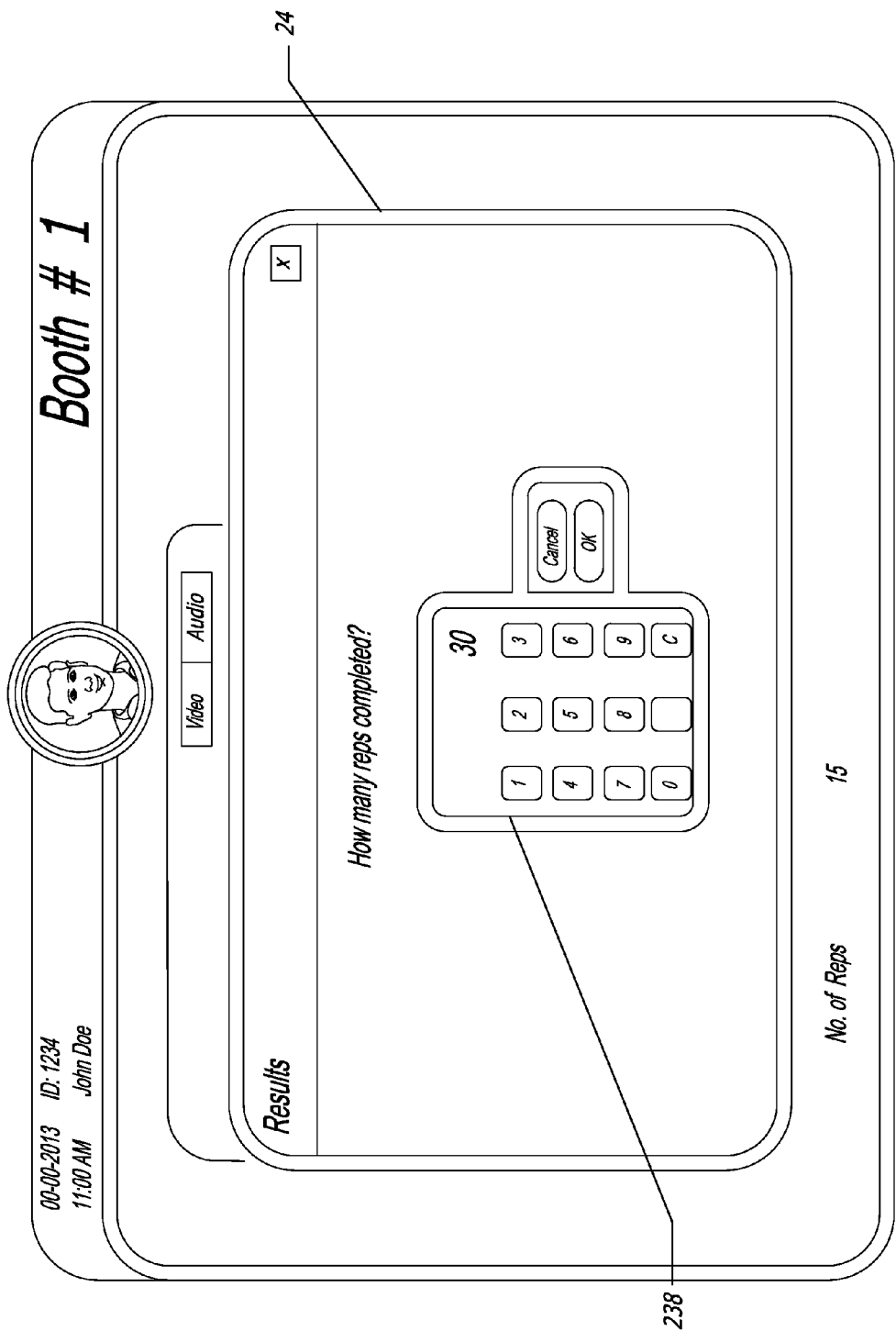
FIG. 29 is a diagrammatic illustration of the electronic screen displaying means for entering a number of exercise repetitions into the computerized system.
Figure 30:
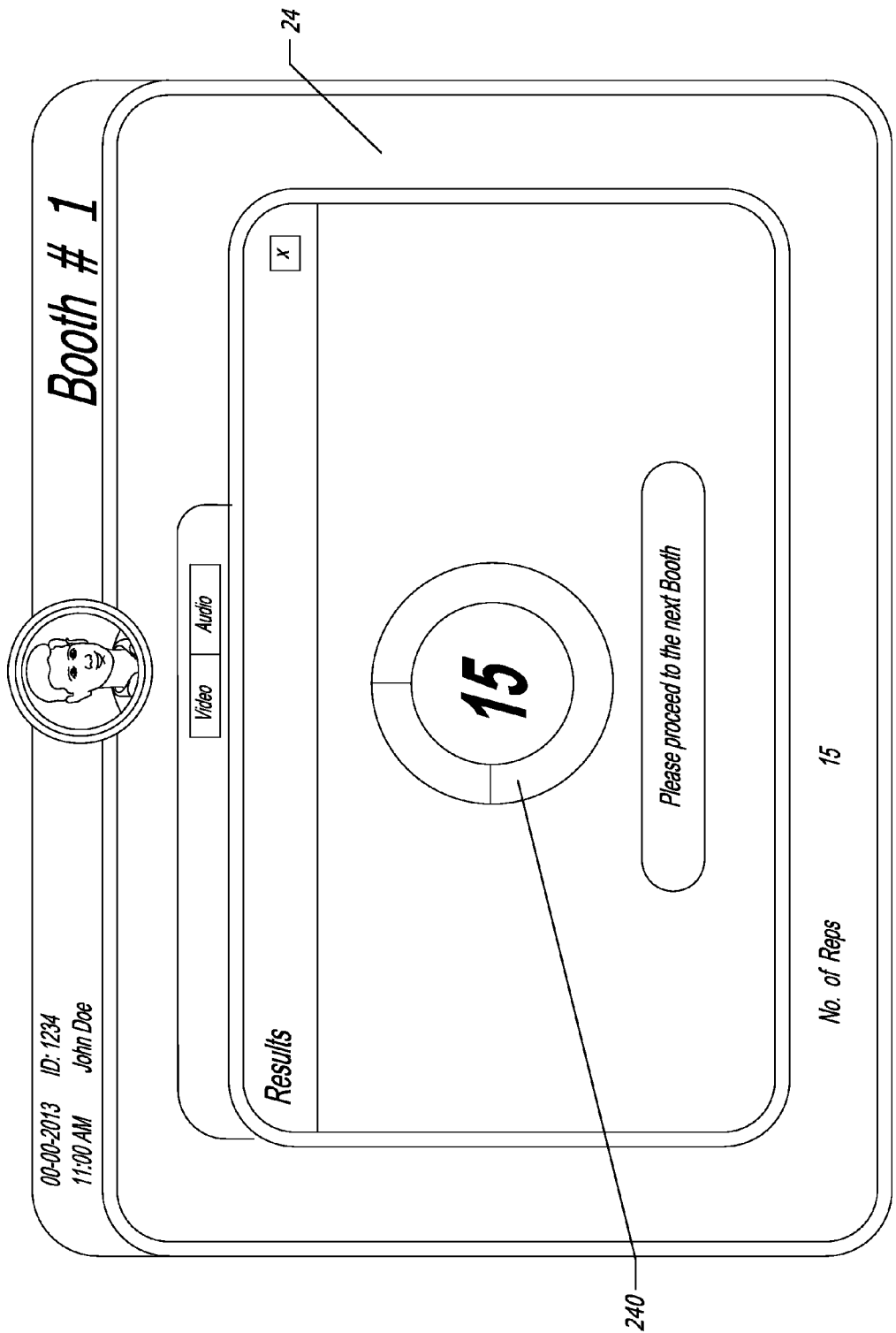
FIG. 30 is a diagrammatic view of an electronic screen displaying a timer to proceed to the next booth and exercise.

With reference to FIG. 29, once the member has performed a given number of reps at the predetermined weight or resistance within the allotted time, the display screen will ask the member to input the number of repetitions completed, such as into the touch keypad 238. As illustrated in FIG. 30, a timer 240 is then provided and the member is prompted to proceed to the next booth in a given set amount of time.

In the example provided in FIGS. 28 and 29, the goal of the member was to perform fifteen repetitions of twenty pounds of the given exercise. FIG. 29 illustrates that the member actually performed thirty repetitions. The system would take that input and consider it for future workouts for that individual. This is accomplished automatically by the computerized system of the present invention, without the need for any operator to enter and analyze data. Instead, the computerized system is configured to simply receive the number of repetitions entered in by each gym member at each exercise station and calculate a new personalized exercise regimen for that member based upon the inputted repetitions at each exercise station. The system would automatically adjust the future number of repetitions and/or weight for that particular exercise.

Of course, the reaction test results for the workout sessions may also be compared and considered. Thus, if the reaction time were essentially the same between the first workout session and the second workout session, the number of repetitions and/or the weight for that particular exercise in booth number one would be increased. The prediction equation could alter the weight and/or the repetitions based upon the desired goals of the member or based upon the inherent prediction equation within the algorithm. However, if the reaction test results were worse the second day, the number of repetitions and/or the weight might not be increased, or might be increased less than what would otherwise be the case if the reaction test results were the same for that member.

Thus, member John Doe upon returning to the gym might be presented with an increased weight of twenty-five pounds to be repeated thirty times, based upon the new calculations from the input provided by John Doe in the previous workout session. Various combinations of weight and repetitions can be made as adjustments to the workout regimen depending upon the prior workout session's input by the member and the daily reaction test results. Thus, for example, if the reaction test results were not as favorable for the subsequent workout, a weight of twenty pounds and a number of repetitions of only twenty-five may be provided to John Doe as the reaction test determined that John Doe was not as mentally and physically alert and capable the morning of the second workout, for example.

Figure 31:
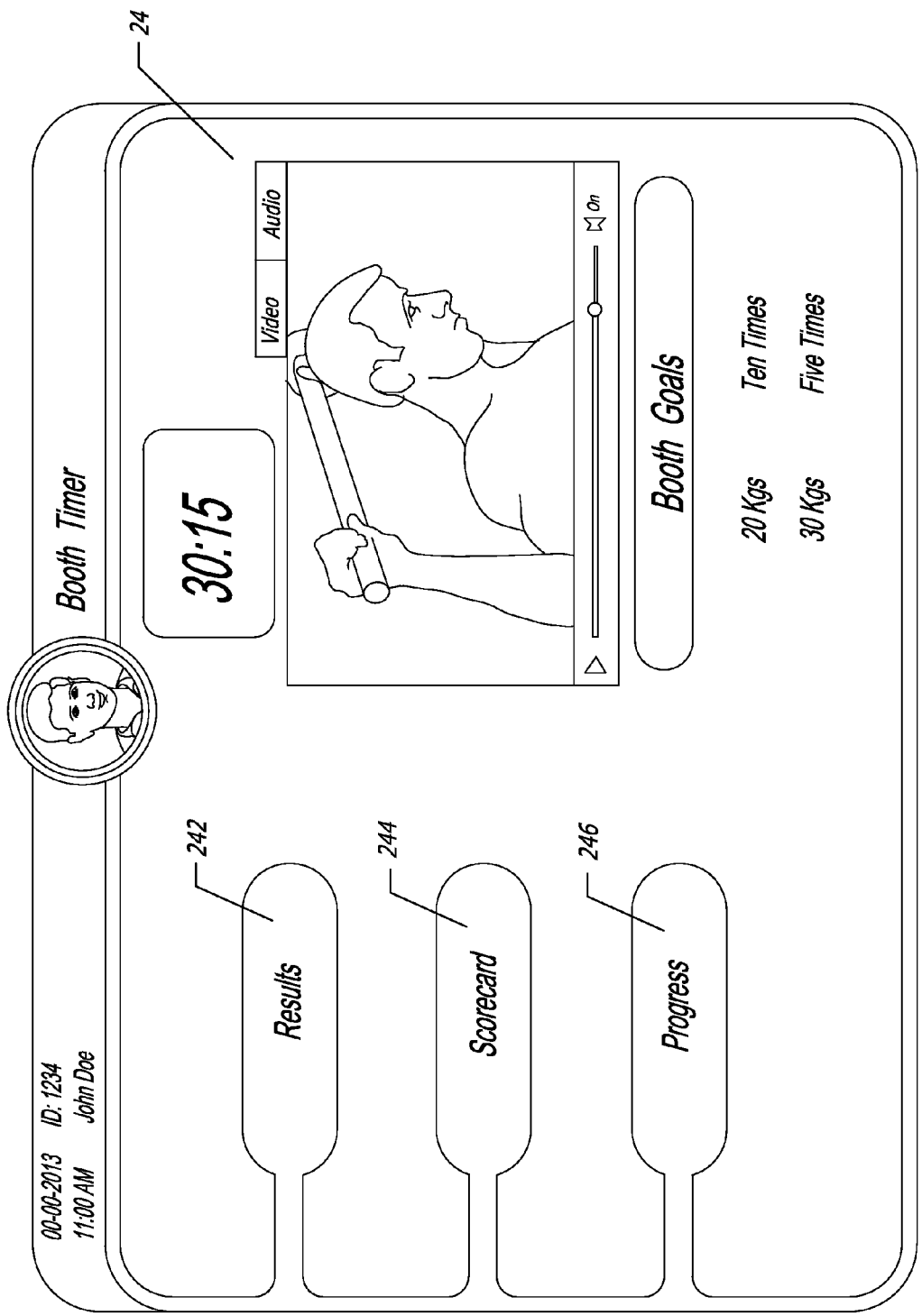
FIG. 31 is a diagrammatic view of a display of an electronic screen providing exercise results of the user.

With reference now to FIG. 31, in the booths which provide a rest period, or otherwise, such as at the end of a workout if sufficient time is provided at the end of an exercise within a given booth, the member is provided a results scorecard and progress screen via the user's computer, smart phone, kiosks within the gym, etc., wherein the member can review the performance of that day's workout session, or even past workout sessions, as illustrated in FIGS. 32 and 33.

For example, at the end of the workout session for the day, either at the gym or at home, the member may be provided a selection of tabs 242-246 in which the user can view the results of a given booth or an overview of the workout regimen for that day, a scorecard tab 244 and a progress tab 246. If the user selects the scorecard tab 244, the member is presented with a scorecard 248 of the results of the various booths completed up to that point that day, or completed in total during the workout session as illustrated in FIG. 32. It can be seen from FIG. 32 that the scorecard 248 provides the user with a summary of the results of the various booths completed, the total number of sessions completed, and the pending sessions yet to be completed. The user can select to review a given exercise or an exercise within a given booth. If the user selects the progress tab 246, a progress chart 250 for the member and showing the number of booths or sessions completed, and the number of sessions or booths remaining, and the time left for the workout regimen is presented to the member, as illustrated in FIG. 33. It is contemplated by the present invention that the member can track performance for a given booth or exercise session over time as a way of viewing progress made in a particular exercise over time.

It will be appreciated that as the member moves from one booth to another, the server and system of the present invention pushes, or has previously pushed, the information relating to that member with respect to the weight or resistance, number of repetitions, etc. for the exercise to be performed in that particular booth. Thus, as the member is directed to move from one booth to another, the display screen will identify and show that member, the stated goals for that particular workout session, and provide an input mechanism at the end of each exercise session, as described above.

It is contemplated by the present invention that as the member enters each booth, the touch screen monitor will not only direct the user as to the exercise prescription of how much work to perform for each exercise, and provide digital photographs or video instruction for demonstration purposes for the exercise or machine, but that the member could choose their own genre of music or select from an existing playlist either provided by the system or their own. The playlist and genre could be selected either during the workout, but more typically prior to the workout.

Each member is provided a customized, personalized workout program for that particular workout day. If the member is scheduled to be in each booth for one minute, the exercise routine for that day would involve approximately thirty minutes by going through thirty booths in the sequence, provided the gym were of a configuration as illustrated in FIG. 15. Indicia, such as the directional arrows illustrated in FIGS. 1-3, can be used to direct the member from one booth to another. The member would provide feedback, as described above, such that the system could adjust and alter the customized workout program for that individual user in the future.

Although the embodiment illustrated and described above includes a touch screen display 24 in each booth, which is interactive so as to accept input from the user, it will be appreciated that any other electronic device may be incorporated into the invention, including kiosks, a keyboard, a mouse, or the like.

Figure 34:
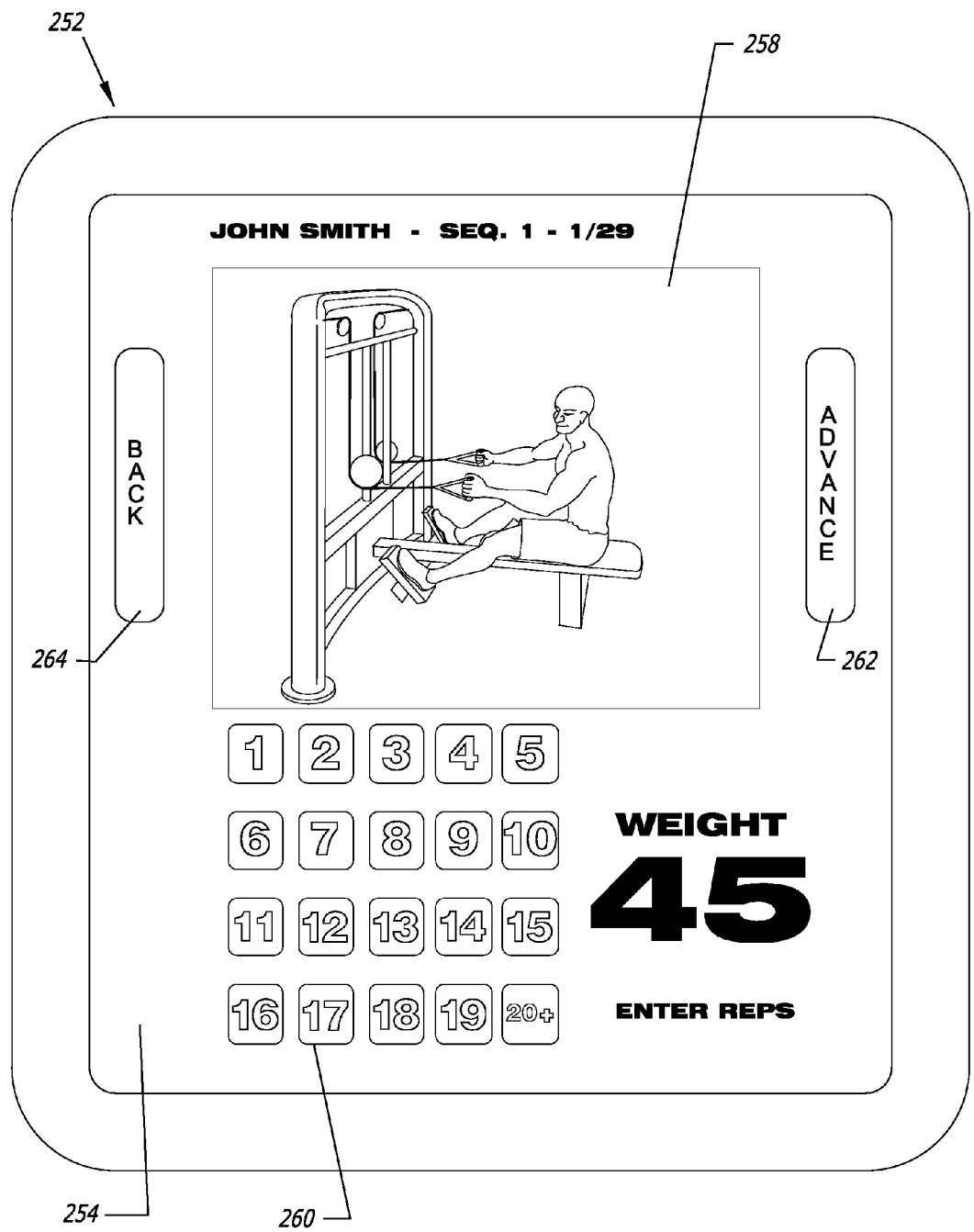
FIG. 34 is a front elevational view of a personal, hand-held electronic device having an electronic screen thereof displaying aspects of a personal exercise regimen, in accordance with the present invention.

In fact, in one embodiment of the present invention, the members could utilize their own personal hand-held electronic device 252, such as a smart phone or tablet, to receive data and provide feedback to the system as to the user's workout performance results, such information being captured and sent via wireless network technology. A computer application is downloaded onto the user's hand-held device 252, such as smart phone, tablet, etc., would perform the same function as the display monitor 24 and the portion of the computer system 34 disposed within each booth 12. An exemplary personal hand-held electronic device 252 is illustrated in FIG. 34. As described above, this can comprise a smart phone, a tablet, or any other personal hand-held device which is capable of downloading a computer application from the computerized system of the invention, displaying the necessary information, and providing interactivity so as to allow the member or user to input exercise performance results into the computerized system through the device.

Using the downloadable computer application, the user arrives at the gym and then with their own portable device, or one provided by the gym, enters their membership number and a PIN number. The device 252 will then automatically download the workout to be performed. This can be downloaded via a wired or wireless network from the server at the gym, or more preferably from a cloud-based computer server.

Figure 35:
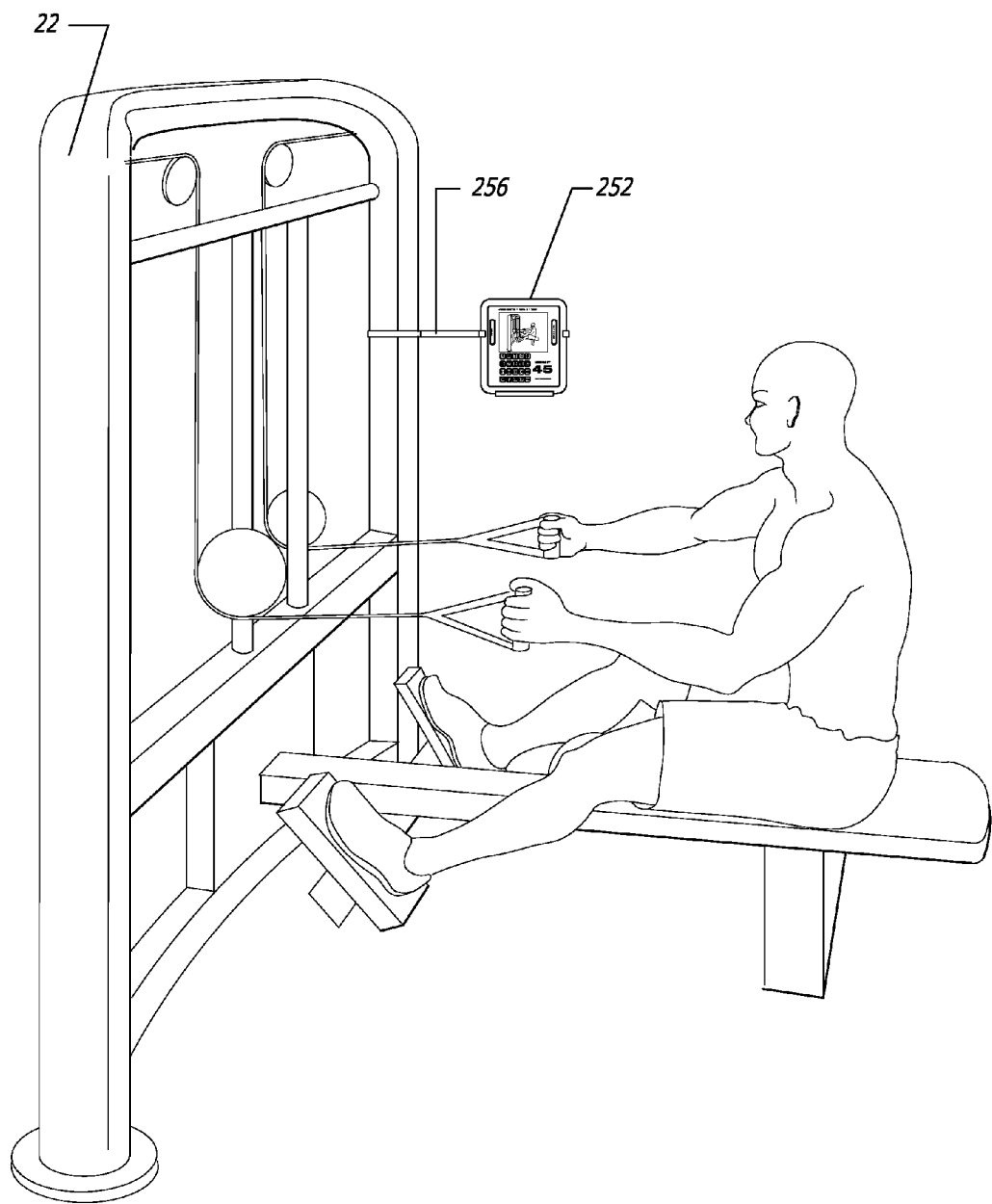
FIG. 35 is a perspective view of a user exercising and viewing the hand-held device of FIG. 34.

The user will then stand at the entrance to the first booth 12 and wait for a queue to enter the first booth. This may be done by either a visual queue or timer on the screen 254 of the user's phone, a visual queue on a monitor outside of the first booth, or an audible prompt generated from a speaker system in the gym. Typically, a countdown is provided to the user to enter the first booth (and each subsequent booth), such as four, three, two, one, advance or the like. At this point, the user enters the booth and places their personal electronic device 252 on a stand or holder 256 positioned such that it can be viewed while performing the exercise, as illustrated in FIG. 35.

A page is downloaded to the hand-held device representing the exercise to be performed in that particular booth. In one embodiment, the hand-held device will automatically sequence for each predetermined time period, such as each minute. In another embodiment, all of the pages representing each of the booths are downloaded onto the hand-held device, and the pages are manually sequenced by the user, such as with a horizontal swipe of the touch screen of the hand-held device.

In the first booth, the hand-held device 252 will display the first page corresponding with the first booth, which has all the information relative to the exercise to be performed in the first booth. An exemplary screen shot or page of the hand-held device is illustrated in FIG. 34. It will be seen that the page of the screen has a number "1" prominently displayed, corresponding to the number posted in the booth. It is anticipated that when the user positions the device on the holder 256 the user will know that they have selected the correct page for the correct booth. For example, the holder or stand 256 may have imprinted, embossed, or otherwise display the booth number. It will also be noted from FIG. 34 that the displayed page includes the name of the user, the selected sequence number of the sequence of pods to perform the workout regimen, and a representation of which booth of the total number of booths the page corresponds to, in this case "1/29".

As shown in FIG. 34, the user has the option to view an animated video or slideshow 258 demonstrating the proper form of the exercise to be performed. Similar to that described above, the weight, resistance, or repetitions to be performed will be displayed on the hand-held device.

Thus, the user enters the booth on the given queue, places their hand-held device in the appropriate holder 256, making sure that the page number matches the number on the holder, and is either shown a tutorial for the exercise or has the option to view the same. Preferably, the stand or holder 256 is positioned such that the user can view the display screen 254 of the personal electronic device 252 while engaging the exercise device 22 and performing the exercise. The user then enters the prescribed and displayed weight on the exercise device 22, and a predetermined time after entering the booth, another queue will indicate that the time has lapsed and the user should stop exercising and enter their score or number of repetitions. Once again, the queue may be an audio queue from the hand-held device or a speaker system within the gym or within the booth, or it may be a visual queue, such as a digital timer, from the hand-held display 254.

As illustrated in FIGS. 34 and 35, via touch pad or keypad 260 or the like, a data entry and interaction with the page is provided to the user. In this manner, the user can enter the number of repetitions performed, compare prior performances, etc., as described above. The user, using the keypad 260 on the hand-held device 252 enters the number of repetitions performed. The information is saved to the device, and will also be relayed, either in real time or at a later time, to the gym computer system or a cloud-based computer system.

An announcement or a timer will then indicate that the user has a certain amount of time left in that particular booth, and then a queue is provided for the user to pick up their hand-held device and proceed to the next booth. The next page corresponding to the next booth is downloaded, or is manually swiped or otherwise selected, as described above. For example, as illustrated in FIG. 34, a touch button 262 may be provided on the touch screen display 254 which advances the page to the next sequence and booth when touched or otherwise selected. Similarly, a back button 264 can be used to go back to a prior page, which represents another exercise and booth within the exercise regimen sequence. The hand-held device is placed in the holder within the second booth and the user confirms that they are in the correct booth by referencing the number on the page and the corresponding number on the holder. The second page gives them the appropriate information for the exercise to be performed in the second booth, as described above with respect to the first booth. This process is repeated through the predetermined number of booths for which the exercise regimen is prescribed. Typically, this is approximately twenty-nine booths, as described above.

Although the information saved to the device may be relayed in real time to the gym's computer system for immediate collection and processing, alternatively, upon exiting the last booth, the user swipes the last page or otherwise selects to send the exercise performance results for that workout regimen to the server, typically via a wireless network to a cloud-based server, where it immediately processes the information, calculating and preparing the user's next prescribed workout regimen according to a predetermined, but alterable algorithm.

It is contemplated by the invention that the downloaded software application to the user's hand-held device 252 will be accessible or usable for a limited period of time. For example, the workout regimen incorporated into the downloaded software application may be used for only one to two hours. Thereafter, the computer application is either removed or otherwise disabled. This prevents confusion with a user inadvertently downloading a workout regimen for a particular day, downloading another workout program for another day and confusing the two. It also prevents a user from downloading a personalized workout regimen generated by the invention's computerized system and utilizing it in a location or in a manner not authorized by those owning the exercise facility or otherwise administering the invention.

Use of the computer application and hand-held device is anticipated to have advantages over the hard-wired computer system. The user can at any time in the future return to the same gym or to any other gym facility supporting the present invention. Once the user enters their membership number and PIN number on the hand-held device, they can choose from any of the sequences available at that particular gym. The gym may have three sequence choices, or more or less. As the information for the individual's workout is pulled from a cloud-based server, the user is able to visit any gym within the world and retrieve their updated personalized workout regimen.

Incorporating the user's hand-held device in the form of a smart phone, tablet, etc., or providing such a device to the user, simplifies the gym arrangement, and does not require the use of individual display monitors within each booth, an individual hard drive, computer system, and networking wires, etc. that are illustrated and described above and that can render the setup of the gym complex and costly.

The individual hand-held devices with the downloaded computer application are less prone to disruptive malfunction. In the case of the server and computer system within the gym relaying information to display monitors within each booth, if there are power surges, loss of power, etc., the entire facility membership will be affected. Whereas, when one user's hand-held device or computer application malfunctions, they will still sequence according to the recorded voice in the gym without disrupting all the other members. They can simply follow a pre-described workout provided to them in orientation explaining how to continue in the event of an application or device malfunction.

With the hard-wired computer system, the system will keep sequence and user data from booth-to-booth oblivious to events or conditions. If someone is disabled in a booth or there is an emergency, the hard-wired computer system continues to advance user data even though the user may not advance. Thus, when the emergency is solved and the sequencing can continue, the computer system may have imported the user's data to several booths ahead of where they are actually at due to the user's inability to advance due to an emergency in another booth within the gym.

However, with the hand-held computer application system, the data stays within the hand-held device in the booth with the user. An operator of the gym facility may announce over the speaker system emergency issues and instructions to the users. For example, the operator may state "there is an issue in sequence number one, all members please patiently stay in the booth you are now in and we will announce your advancement soon". As soon as the issue is resolved, the operator may announce on the next announcement or queue "please advance to the next booth".

Moreover, the computer application system could be used outside of the personal booth sequencing system. For example, in addition to the sequencing system, there could be a generic workout. A predetermined number of pages, such as twenty-nine pages, may prescribe twenty-nine exercises to be performed in sequence at any given gym on generic equipment. Although this might be complicated by the fact that the particular exercise equipment might not be readily available to the user within a gym that does not have the private booths and sequencing system illustrated and described above, it would allow the user to perform the personalized and updated exercise regimen to be performed at any gym, while saving the user's results and subsequently updating the user's exercise regimen for the next workout.

It is contemplated by the present invention that although the booths are used in accordance with the workout sequencing program indicated above, the booths instead could be used for other exercise programs. For example, a set of booths could be directed to upper body muscle groups, while another set of booths could be directed to lower body exercises, while yet another set of booths could be directed to core muscle groups, as an example. While this arrangement may not provide an optimal full body exercise regimen, it may be more desirable to some users. The concept of utilizing private booths could also be extended to other types of exercises, such as cardiovascular exercise machines, wherein each booth contains a separate treadmill, stationary bike, elliptical machine, etc. such that the user is able to perform that exercise for the prescribed or desired amount of time in a private setting, while still attending a public gym, and thus obtaining the benefits of a public workout session.

It will be appreciated that the present invention provides many advantages over current methodologies and systems. The automatically generated personalized workout provides the user with a directed workout, and allows the user to relax and have direction. There is no question as to which exercise to do next. The system simply tells the user what exercise to do, for how many repetitions and weight/resistance, and there is no thought required as to which exercise to perform next. This results in less stress, and no waiting time for equipment. The customer may have the sense that the facility was built specifically for their own personal experience. The privacy aspect of the booths also reduces stress and distractions and allows for better concentration and a more effective workout. The booths are adaptable to the contour and layout of the building, and can be interchangeable. The booths can also present a protected environment with reduced exposure to airborne communicable diseases. Use of the booth system allows the facility to accommodate all of its users, whereas traditional gyms can only handle approximately sixty percent (60%) of their members at any given time. This is due to the fact that the users of the present invention select and book a particular time for their workout, and will know that each of the booths and exercises will be available to them at that time. However, if a large number of members of a traditional gym were to visit the gym at a particular time, those users may need to wait to access equipment and work stations. The present invention is automated, without the need of data entry or computer programs to assess and enter data. No computer data operators, or even trainers are necessary. This slashes the number of people required to run a gym dramatically. Furthermore, in a gym with as few as three sequences, three members can start every minute, or one hundred eighty members per hour. These members may not see any other members or have any interaction with them during their entire workout regimen, yet receive a highly optimized workout due to the exercise science and computerized system incorporated into the invention. Essentially, the gym member is receiving the services of his or her own personal trainer or exercise physiologist without the need of hiring one of these individuals or scheduling a time with one of these individuals or working out with one of these individuals. These inherent services within the system of the present invention could enable the gym to charge higher fees than traditional gyms.

Although several embodiments have been described in detail for purposes of illustration, various modifications may be made without departing from the scope and spirit of the invention. Accordingly, the invention is not to be limited, except as by the appended claims.

What is claimed is:

1. A personal training system, comprising:
a plurality of booths arranged in a predetermined sequence, each booth having an entry and an exit and each booth configured to be used by a single user at a time and provide privacy to the user thereof, each booth being assigned an exercise and having exercise equipment therein for performing the assigned exercise;
a computerized system for generating a exercise regimen for each of a plurality of user's, the exercise regimen comprising a plurality of exercises to be performed in sequence according to the predetermined sequence of the plurality booths;
at least one electronic device for directing the users to perform each exercise within each booth according to the exercise regimen sequence generated by the computerized system for the users; and
means for notifying the users to move to the next booth in the predetermined sequence of booths to perform the next exercise in the users exercise regimens.

2. The system of claim 1, wherein the notifying means comprises an electronic device that directs the users to substantially simultaneously move from one booth to another in a predetermined sequence in order to complete the user's exercise regimen.

3. The system of claim 1, wherein the at least one electronic device provides a time limit for the user to perform the exercise within the booth.

4. The system of claim 1, wherein each of the booths is assigned a warmup or stretch exercise, a vibration exercise, a push exercise, a pull exercise, a rotate exercise, or a full body exercise.

5. The system of claim 1, wherein the at least one electronic device comprises an electronic screen for displaying information relating to the exercise to be performed by the user.

6. The system of claim 5, wherein the electronic screen displays user identification, a tutorial for the exercise, and a performance goal for the user for the exercise and a timer.

7. The system of claim 6, wherein the user performance results are input into the computerized system using the electronic screen.

8. The system of claim 6, wherein the exercise performance goal for the user comprises a goal number of repetitions of the exercise to be performed by the user within a predetermined time period.

9. The system of claim 8, wherein the exercise performance goal for the user further comprises a resistance or a weight to be used during the exercise by the user.

10. The system of claim 1, wherein the at least one electronic device comprises a touch screen display disposed within each booth.

11. The system of claim 1, wherein the at least one electronic device comprises a portable personal electronic device having an electronic display screen and means for inputting data.

12. The system of claim 1, wherein user performance results are inputted into the computerized system for each exercise performed by the user, and wherein the computerized system automatically adjusts the user's exercise regimen according to the user's performance results input into the computerized system.

13. The system of claim 1, wherein the notifying means comprises a timer for alerting and directing the users to move from one booth to another in the predetermined sequence after a predetermined period of time has lapsed.

14. The system of claim 1, wherein the booths are interconnected and allow the users to move from one booth to an adjacent booth.

15. The system of claim 14, wherein in at least a plurality of the booths the entry of a booth comprises the exit of an adjacent booth.

16. An exercise facility, comprising:
a plurality of booths within the exercise facility arranged in a predetermined sequence, each booth defining an enclosed space adapted to be used by a single user at a time and configured to provide privacy to the user while in the booth, each booth having assigned thereto a predetermined exercise to be performed by the user within the booth, wherein the plurality of booths are interconnected with one another to allow users to move from one booth to an adjacent booth;
a computerized system for generating a exercise regimen for each of a plurality of user's comprised of a plurality of exercises to be performed in sequence according to the predetermined sequence of the plurality of booths;
an electronic device including a display screen for displaying information relating to the exercise to be performed within each booth; and
means for notifying the user that the time allotted for the exercise within the booth has expired and for the users to substantially simultaneously move to the next booth in the sequence of booths to perform the next exercise in the users exercise regimens.

17. The exercise facility of claim 16, including exercise devices disposed within a plurality of the booths for performing the assigned exercises within those booths.

18. The exercise facility of claim 16, including means within each booth for inputting exercise performance results of the user into the computerized system.

19. The exercise facility of claim 18, wherein the computerized system automatically adjusts the user's exercise regimen based on the user's exercise performance results.

20. The system of claim 16, wherein the notifying means comprises an electronic device or timer.

* * * * *